(12) United States Patent
Anderson et al.

(10) Patent No.: US 8,734,437 B2
(45) Date of Patent: May 27, 2014

(54) CATHETER HAVING ELECTRICALLY CONDUCTIVE PATHWAYS

(75) Inventors: James M. Anderson, Fridley, MN (US); Karl A. Jagger, Deephaven, MN (US); Allen Delander, Maple Grove, MN (US); Richard R. Miller, Anoka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1146 days.

(21) Appl. No.: 12/178,451

(22) Filed: Jul. 23, 2008

(65) Prior Publication Data

US 2010/0022950 A1 Jan. 28, 2010

(51) Int. Cl.
*A61B 18/04* (2006.01)
*A61M 25/00* (2006.01)
*A61M 37/00* (2006.01)
*A61M 31/00* (2006.01)

(52) U.S. Cl.
USPC ........... 606/32; 604/509; 604/264; 604/95.03

(58) Field of Classification Search
USPC .............................. 604/32–34, 264
See application file for complete search history.

(56) References Cited

U.S. PATENT DOCUMENTS

| | | | |
|---|---|---|---|
| 3,428,046 A * | 2/1969 | Vagenius et al. | 604/265 |
| 4,484,586 A | 11/1984 | McMickle et al. | |
| 5,334,169 A | 8/1994 | Brown et al. | |
| 5,725,817 A | 3/1998 | Milder | |
| 5,807,306 A * | 9/1998 | Shapland et al. | 604/21 |
| 6,017,335 A * | 1/2000 | Burnham | 604/527 |
| 6,213,995 B1 | 4/2001 | Steen et al. | |
| 2008/0015517 A1 | 1/2008 | Geistert et al. | |

FOREIGN PATENT DOCUMENTS

WO 02/055145 A1 7/2002

* cited by examiner

*Primary Examiner* — Jason Flick
*Assistant Examiner* — Rebecca E Eisenberg
(74) *Attorney, Agent, or Firm* — Seager, Tufte & Wickhem LLC

(57) ABSTRACT

Medical devices having electrically conductive pathways are disclosed. More particularly, the disclosure is directed to catheter shafts including an electrically conductive wire embedded in a polymeric tube. The disclosure is also directed to catheter shafts including an electrically conductive media coextruded in a polymeric tube. The disclosure is also directed to catheter shafts including electrically conductive pathways formed with electrically conductive ink, paste, adhesive and/or epoxy.

12 Claims, 20 Drawing Sheets

CATHETER HAVING ELECTRICALLY CONDUCTIVE PATHWAYS

TECHNICAL FIELD

The disclosure is directed to medical devices having electrically conductive pathways. More particularly, the disclosure is directed to catheter shafts including an electrically conductive wire embedded in a polymeric tube. The disclosure is also directed to catheter shafts including an electrically conductive media coextruded in a polymeric tube. The disclosure is also directed to catheter shafts including electrically conductive pathways formed with electrically conductive ink, paste, adhesive and/or epoxy.

BACKGROUND

During medical procedures, it may be advantageous to use an interventional device which is electrically integrated. However, such an interventional device requires an electrical pathway to provide electrical conduction through the interventional device. Therefore, a need remains for interventional medical devices including electrically conductive pathways providing electrical current/voltage to an electrically activated/responsive working element. For instance, in may be desirable to provide an elongate medical device (e.g., catheter, guidewire, etc.) with an electrically conductive pathway extending from a proximal region of the elongate medical device to a distal region of the elongate medical device. The electrically conductive pathway may supply electrical current/voltage to a working element of the elongate medical device and/or provide a pathway for sending/receiving an electrical signal through the elongate medical device.

SUMMARY

The disclosure is directed to several alternative designs, materials and methods of manufacturing medical device structures and assemblies.

Accordingly, one illustrative embodiment is a medical catheter comprising:
an elongate tubular member having a central longitudinal axis, the elongate tubular member including an annular wall having an inner surface and an outer surface;
one or more electrically conductive pathways embedded within the annular wall of the elongate tubular member and extending parallel to the central longitudinal axis of the elongate tubular member from a proximal region of the elongate tubular member to a distal region of the elongate tubular member;
wherein the annular wall of the elongate tubular member in which the one or more electrically conductive pathways is/are embedded is a single layer of polymeric material having a continuous molecular structure.

Another illustrative embodiment is an extrusion system for extruding an electrically conductive member in a polymeric tube, the extrusion system including:
an extrusion head having an outlet opening;
an extrusion die located within the extrusion head, the extrusion die including a body extending from a rear end of the extrusion die to a forward end of the extrusion die, the extrusion die including a central bore extending from the rear end to the forward end of the extrusion die, and one or more lumens radially arranged around the central bore; and
one or more electrically conductive members extending into the central bore of the extrusion die from the rear end of the extrusion die, and extending out of the one or more lumens from the forward end of the extrusion die.

Another illustrative embodiment is an extrusion die comprising:
a body including a generally cylindrical portion having a first diameter, a nose having a second diameter less than the first diameter, and a tapered portion between the generally cylindrical portion and the nose;
the body including a central bore having a central longitudinal axis extending through the body;
the nose including an annular wall defining a central opening having a central longitudinal axis aligned with the central longitudinal axis of the central bore;
the nose further including one or more wire lumens in the annular wall and extending parallel to the central longitudinal axis of the central opening; and
the nose further including one or more side openings extending from an exterior surface of the nose into the central opening of the nose.

Another illustrative embodiment is a method of extruding a tubular member having an electrically conductive member embedded therein, the method comprising:
providing an extrusion die, the extrusion die including a body having a first diameter, which tapers down to a nose having a second diameter, the nose including a central opening having a longitudinal axis and one or more side openings extending radially inward into the central opening from a exterior surface of the nose, the extrusion die including a central bore longitudinally aligned with the central opening of the nose, the nose further including one or more lumens radially arranged around the central opening of the nose and extending parallel to the longitudinal axis of the central opening;
feeding one or more electrically conductive members through the one or more lumens of the nose; and
flowing a polymeric material both around the exterior surface of the nose and through the central opening of the nose;
wherein as the polymeric material leaves the extrusion die, a portion of the polymeric material is located radially inward of the one or more electrically conductive members and a portion of the polymeric material is located radially outward of the one or more electrically conductive members.

Another illustrative embodiment is a method of extruding a catheter shaft having an electrically conductive member embedded therein, the method comprising:
providing an extrusion head and an extrusion die housed within the extrusion head;
feeding a plurality of electrically conductive wires into the extrusion head and through the extrusion die; and
extruding a polymeric material from the extrusion head, wherein a portion of the polymeric material is extruded around an exterior portion of the extrusion die and a portion of the polymeric material is extruded within an interior portion of the extrusion die;
wherein at the moment the polymeric material leaves the extrusion head, the plurality of electrically conductive wires are embedded in the polymeric material.

Another illustrative embodiment is a method of forming a tubular member including an electrically conductive pathway, the method comprising:
extruding a polymeric tubular member, the tubular member having an annular wall having an outer surface and an inner surface, wherein the annular wall of the tubular member includes one or more longitudinal recesses extending longitudinally along the tubular member, wherein the one or more longitudinal recesses extend inward from the outer surface of the annular wall;

placing an electrically conductive member in the one or more longitudinal recesses of the annular wall of the tubular member; and disposing an outer layer of polymeric material over the tubular member and the electrically conductive member, such that an inner surface of the outer layer is in contact with the outer surface of the tubular member.

Another illustrative embodiment is a medical catheter comprising:

an elongate shaft having a proximal end and a distal end;

a first electrically conductive pathway extending along the elongate shaft from a proximal region of the elongate shaft proximate the proximal end of the elongate shaft to a distal region of the elongate shaft proximate the distal end of the elongate shaft;

a second electrically conductive pathway extending along the elongate shaft from the proximal region of the elongate shaft proximate the proximal end of the elongate shaft to the distal region of the elongate shaft proximate the distal end of the elongate shaft; and a pressure sensing tip located at the distal end of the elongate shaft, the pressure sensing tip including:
 a first layer of electrically conductive ink in electrical contact with the first electrically conductive pathway;
 a second layer of electrically conductive ink in electrical contact with the second electrically conductive pathway; and
 one or more layers of pressure variable resistor ink interposed between the first layer of electrically conductive ink and the second layer of electrically conductive ink;
 wherein electrical resistance across the pressure variable resistor ink is dependent on pressure applied to the pressure sensing tip.

Another illustrative embodiment is a medical catheter comprising:

an elongate shaft having a proximal end and a distal end;

an electrically activated/responsive working element located proximate the distal end of the elongate shaft; and an electrically conductive pathway extending along the exterior of the elongate shaft from a proximal region of the elongate shaft proximate the proximal end of the elongate shaft to a distal region of the elongate shaft proximate the distal end of the elongate shaft;

the electrically conductive pathway comprising a layer of an electrically conductive ink applied along the elongate shaft;

wherein electrical current may be supplied to the electrically activated/responsive working element by the electrically conductive pathway.

Another illustrative embodiment is a medical catheter comprising:

an elongate shaft having a proximal end and a distal end;

a first electrically conductive pathway extending along the elongate shaft from a proximal region of the elongate shaft proximate the proximal end of the elongate shaft to a distal region of the elongate shaft proximate the distal end of the elongate shaft;

a second electrically conductive pathway extending along the elongate shaft from the proximal region of the elongate shaft proximate the proximal end of the elongate shaft to the distal region of the elongate shaft proximate the distal end of the elongate shaft;

an inflation balloon secured to the elongate shaft proximate the distal end of the elongate shaft; and a layer of pressure variable resistor ink applied to the exterior surface of the inflation balloon, the layer of pressure variable resistor ink being electrically coupled to the first electrically conductive pathway and the second electrically conductive pathway;

wherein electrical resistance across the pressure variable resistor ink is dependent on pressure applied to the inflation balloon.

Another illustrative embodiment is a medical catheter comprising:

an elongate shaft having a proximal end and a distal end;

a first electrically conductive pathway extending along the elongate shaft from a proximal region of the elongate shaft proximate the proximal end of the elongate shaft to a distal region of the elongate shaft proximate the distal end of the elongate shaft;

a second electrically conductive pathway extending along the elongate shaft from the proximal region of the elongate shaft proximate the proximal end of the elongate shaft to the distal region of the elongate shaft proximate the distal end of the elongate shaft; and a strain gauge located in the distal region of the elongate shaft and electrically connected to the first electrically conductive pathway and the second electrically conductive pathway, the strain gauge including:
 a substrate layer bondable to the elongate shaft;
 a serpentine layer of electrically conductive ink deposited on the substrate layer; and
 a layer of pressure variable resistor ink deposited on the layer of electrically conductive ink;
 wherein electrical resistance across the pressure variable resistor ink is dependent on strain experienced by the strain gauge.

Another illustrative embodiment is a method of creating an electrically conductive pathway along a medical catheter, the method comprising:

a) providing a stereotype plate including a channel;

b) filling the channel of the stereotype plate with an electrically conductive ink;

c) pressing a pad against the stereotype plate into contact with the electrically conductive ink;

d) removing the pad from the stereotype plate, wherein the electrically conductive ink is transferred from the channel to the pad;

e) bringing the pad into contact with a portion of a medical catheter such that the electrically conductive ink contacts the medical catheter; and f) transferring the electrically conductive ink from the pad to the medical catheter.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
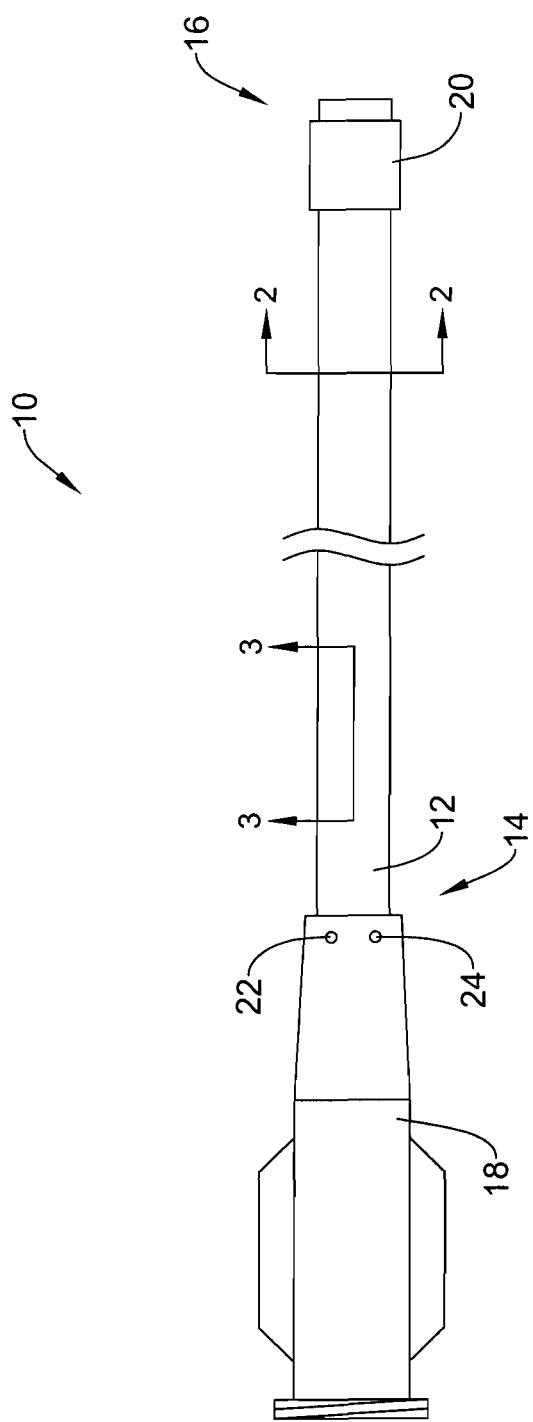
FIG. 1 is a plan view of an exemplary catheter.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring to FIG. 1, there is shown an exemplary catheter 10. The catheter 10 may include an elongate shaft 12 extending from a proximal end 14 to a distal end 16. The proximal end 14 of the elongate shaft 12 of the catheter 10 may extend into and/or be secured to a hub assembly 18. The hub assembly 18 may provide access to one or more, or a plurality of lumens extending through the elongate shaft 12 of the catheter 10.

The distal end 16 of the elongate shaft 12 of the catheter 10 may include a working element 20 utilizing electrical current/voltage during operation. For example the working element 20 may be an electrical cauterization device, an electrolysis device, an electrolysis controlled drug eluting balloon and/or stent, electrodes, a thermal ablation device, a radio frequency device, an ultrasonic device (e.g., ultrasonic transducer), an electroportation device, a device incorporating electro-active polymer (EAP), NG detachable coils, a brachy therapy radiation device, a micro-perfusion pump, an infrared device, an atherectomy device, an electro-active neurovascular coil, a sensor such as a temperature, flow, force, strain, or pressure sensor, or other working element utilizing an electrical current/voltage to perform a medical procedure or treatment within a patient's body.

The catheter 10 may include an electrically conductive pathway extending from a proximal region of the catheter 10 which remains exterior of a patient during a medical procedure to a distal region of the catheter 10 which may be located within a patient during a medical procedure. The catheter 10 may include one or more, or a plurality of electrical terminals in electrical contact with one or more or a plurality of electrically conductive pathways of the catheter 10. For example, the catheter 10 may include a first electrical terminal 22 in electrical contact with one or more electrically conductive pathways. The catheter 10 may include a second electrical terminal 24 in electrical contact with one or more electrically conductive pathways. In some embodiments, the catheter 10 may include additional electrical terminals, for example, a third, fourth, fifth, and/or sixth electrical terminal in electrical contact with one or more electrically conductive pathways. As shown in FIG. 1, in some embodiments the electrical terminals 22/24 may be located in the hub assembly 18 of the catheter 10. In other embodiments, the electrical terminals 22/24 may be located in the elongate shaft 12, may extend from the elongate shaft 12, may extend from the hub assembly 18, or another desired location.

The electrically conductive pathway(s) may extend distally from the electrical terminals 22/24 to the working element 20 to provide an electrical current/voltage to the working element 20 during a medical procedure. For example, during a medical procedure, an electrical current/voltage may be passed distally by an electrically conductive pathway from the first terminal 22 to the working element 20, and the electrical current/voltage may be passed back proximally by another electrically conductive pathway from the working element 20 to the second terminal 24. A power source may be electrically connected to the terminals 22/24 to provide an electrical current/voltage to the working element 20 during a medical procedure.

Figure 2B:
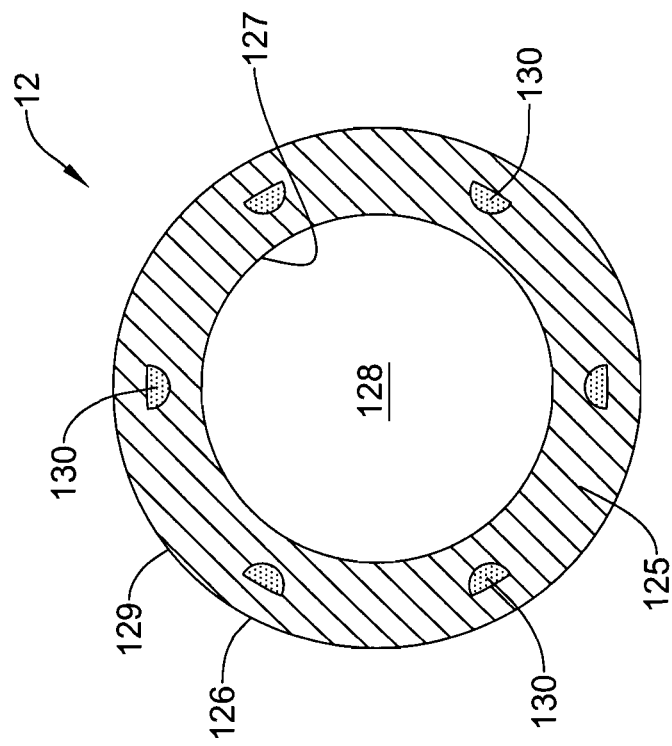
FIG. 2B is an alternative transverse cross-sectional view of the catheter shaft taken along line 2-2 of FIG. 1.
Figure 2A:
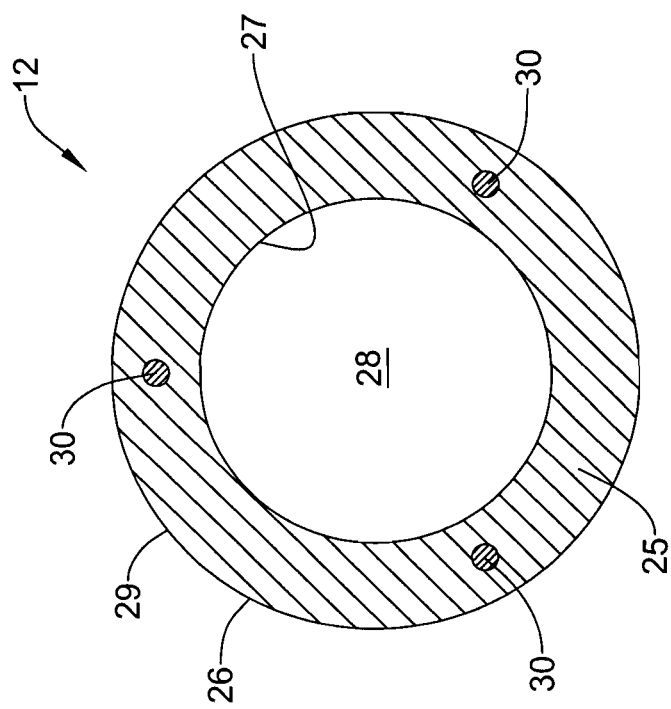
FIG. 2A is a transverse cross-sectional view of the catheter shaft taken along line 2-2 of FIG. 1.

FIG. 2A is a transverse cross-sectional view of the elongate shaft 12 of the catheter 10 taken along line 2-2 of FIG. 1. As shown in FIG. 2A, the elongate shaft 12 may include a tubular member 26 having an inner surface 27 and an outer surface 29. The inner surface 27 of the tubular member 26 defines a lumen 28 extending through the tubular member 26. In some embodiments, the lumen 28 may extend from the proximal end 14 to the distal end 16 of the elongate shaft 12.

The tubular member 26 may include one or more, or a plurality of electrically conductive pathways, such as electrically conductive wires 30 embedded in the wall 25 of the tubular member 26. In some embodiments, the wall 25 may be an annular wall. The electrically conductive wires 30 may be embedded in the wall 25 of the tubular member 26 such that the electrically conductive wires 30 are positioned radially inward from the exterior surface 29 of the tubular member 26 and/or radially outward from the interior surface 27 of the tubular member 26. In other words, a portion of the wall 25 of the tubular member 26 may be positioned radially outward of the electrically conductive wires 30 and/or a portion of the wall 25 of the tubular member 26 may be positioned radially inward of the electrically conductive wires 30. Thus, in some embodiments the electrically conductive wires 30 may be entirely surrounded by the wall 25 of the tubular member 26.

The wall 25 of the tubular member 26 may be a monolithic layer (i.e., formed of a single layer of a continuous molecular structure). In other words, the wall 25 in which the electrically conductive wires 30 are embedded may be a single layer of polymeric material having a continuous molecular structure. In some embodiments, the polymeric material forming the monolithic layer may be a homogenous polymeric material, or the polymeric material forming the monolithic layer may be a heterogeneous polymeric material.

As will be described while referring to FIGS. 4, 5 and 5A-5D, in some embodiments the electrically conductive wires 30 may be embedded within the wall 25 of the tubular member 26 during an extrusion process. Thus, the portions of the wall 25 radially interior and radially exterior of the conductive wires 30 may be simultaneously formed around the electrically conductive wires 30, forming a single layer of continuous molecular structure surrounding the electrically conductive wires 30.

In some embodiments, the electrically conductive wires 30 may be formed of titanium or titanium alloys, stainless steel alloys, copper or copper alloys, silver or silver alloys, gold or gold alloys, platinum or platinum alloys, tungsten or tungsten alloys, magnesium or magnesium alloys, carbon or carbon alloys, or nickel alloys such as nickel-chromium-molybdenum alloys (e.g., UNS: N06625 such as INCONEL® 625). However, in some embodiments, other conductive materials may be used to form the electrically conductive wires 30.

In some embodiments, the tubular member 26 may be formed of polyamide, polyethylene, polypropylene, polystyrene, polyurethane, polyethylene, nylon, polycarbonate, fluoroplastic, fluoropolymer, thermoplastic elastomer such as C-FLEX®, a thermoplastic polyurethane elastomer such as TECOTHANE®, TECOFLEX® or TEXIN®, a thermoplastic polyester elastomer such as HYTREL®, or a mixture, a blend or a co-polymer thereof.

For exemplary purposes, in some embodiments the outer diameter of the tubular member 26 may be about 0.082 inches, and the inner diameter of the tubular member 26 may be about 0.060 inches. Thus, the thickness of the wall 25 of the tubular member 26 may be about 0.012 inches. The cross-sectional dimension (e.g., diameter) of the electrically conductive wires 30 may be about 0.002 inches in some embodiments. It is noted, however, that these dimensions are provided for illustrative purposes; dimensions may deviate from those indicated above.

It is noted that although the tubular member 26 is shown as including a single layer of material, in some embodiments the tubular member 26 may include one or more additional layers of material interior of the wall 25 and/or exterior of the wall 25 of the tubular member 26. For example, an inner lubricious layer, such as a layer of polytetrafluoroethylene (PTFE) or polyvinylidene fluoride (PVDF), may be located radially inward from the inner surface 27 of the tubular member 26 and/or an outer covering may be located radially outward from the outer surface 29 of the tubular member 26.

FIG. 2B is an alternative transverse cross-sectional view of the elongate shaft 12 of the catheter 10 taken along line 2-2 of FIG. 1. As shown in FIG. 2B, the elongate shaft 12 may include a tubular member 126 having an inner surface 127 and an outer surface 129. The inner surface 127 of the tubular member 126 defines a lumen 128 extending through the tubular member 126. In some embodiments, the lumen 128 may extend from the proximal end 14 to the distal end 16 of the elongate shaft 12.

The tubular member 126 may include one or more, or a plurality of electrically conductive pathways, such as electrically conductive media 130 embedded in the wall 125 of the tubular member 126. In some embodiments, the wall 125 may be an annular wall. The electrically conductive media 130 may be embedded in the wall 125 of the tubular member 126 such that the electrically conductive media 130 is positioned radially inward from the outer surface 129 of the tubular member 126 and/or radially outward from the inner surface 127 of the tubular member 126. In other words, a portion of the wall 125 of the tubular member 126 may be positioned radially outward of the electrically conductive media 130 and/or a portion of the wall 125 of the tubular member 126 may be positioned radially inward of the electrically conductive media 130. Thus, in some embodiments the electrically conductive media 130 may be entirely surrounded by the wall 125 of the tubular member 126.

The wall 125 of the tubular member 126 may be a monolithic layer (i.e., formed of a single layer of a continuous molecular structure). In other words, the wall 125 in which the electrically conductive media 130 is embedded may be a single layer of polymeric material having a continuous molecular structure. In some embodiments, the polymeric material forming the monolithic layer may be a homogenous polymeric material, or the polymeric material forming the monolithic layer may be a heterogeneous polymeric material.

In some embodiments, the electrically conductive media 130 may be embedded within the wall 125 of the tubular member 126 during an extrusion process, such as a co-extrusion process. For example, the electrically conductive media 130 may be simultaneously extruded, or otherwise disposed within the wall 125 of the tubular member 126, during the extrusion of the tubular member 126. Thus, the portions of the wall 125 radially interior and radially exterior of the electrically conductive media 130 may be simultaneously formed around the electrically conductive media 130, forming a single layer of continuous molecular structure surrounding the electrically conductive media 130.

The electrically conductive media 130 may be any desired media which is electrically conductive. In some embodiments, the electrically conductive media 130 may be a conductive ink, a conductive powder, a conductive paste, a conductive epoxy, a conductive adhesive, a conductive polymer or polymeric material, or other conductive material. For example, the electrically conductive media 130 may include about 0.5% to about 40%, about 1% to about 30%, or about 10% to about 30% by weight of metallic particles suspended in a generally non-conductive medium. For instance, in some embodiments, the electrically conductive media 130 may include silver, gold, platinum, carbon, stainless steel, or magnesium particles suspended in a generally non-conductive medium. In some embodiments, the non-conductive medium may be a polymeric material, a ceramic material, an ink, an epoxy, an adhesive, or other desired material. The presence of the electrically conductive particles in the generally non-conductive medium may provide the electrically conductive media 130 with adequate conductivity to pass an electrical current along the electrically conductive media 130.

In some embodiments, the tubular member 126 may be formed of polyamide, polyethylene, polypropylene, polystyrene, polyurethane, polyethylene, nylon, polycarbonate, fluoroplastic, fluoropolymer, thermoplastic elastomer such as C-FLEX®, a thermoplastic polyurethane elastomer such as TECOTHANE®, TECOFLEX® or TEXIN®, a thermoplastic polyester elastomer such as HYTREL®, or a mixture, a blend or a co-polymer thereof.

It is noted that although the tubular member 126 is shown as including a single layer of material, in some embodiments the tubular member 126 may include one or more additional layers of material interior of the wall 125 and/or exterior of the wall 125 of the tubular member 126. For example, an inner lubricious layer, such as a layer of polytetrafluoroethylene (PTFE) or polyvinylidene fluoride (PVDF), may be located radially inward from the inner surface 127 of the tubular member 126 and/or an outer covering may be located radially outward from the outer surface 129 of the tubular member 126.

Figure 3A:
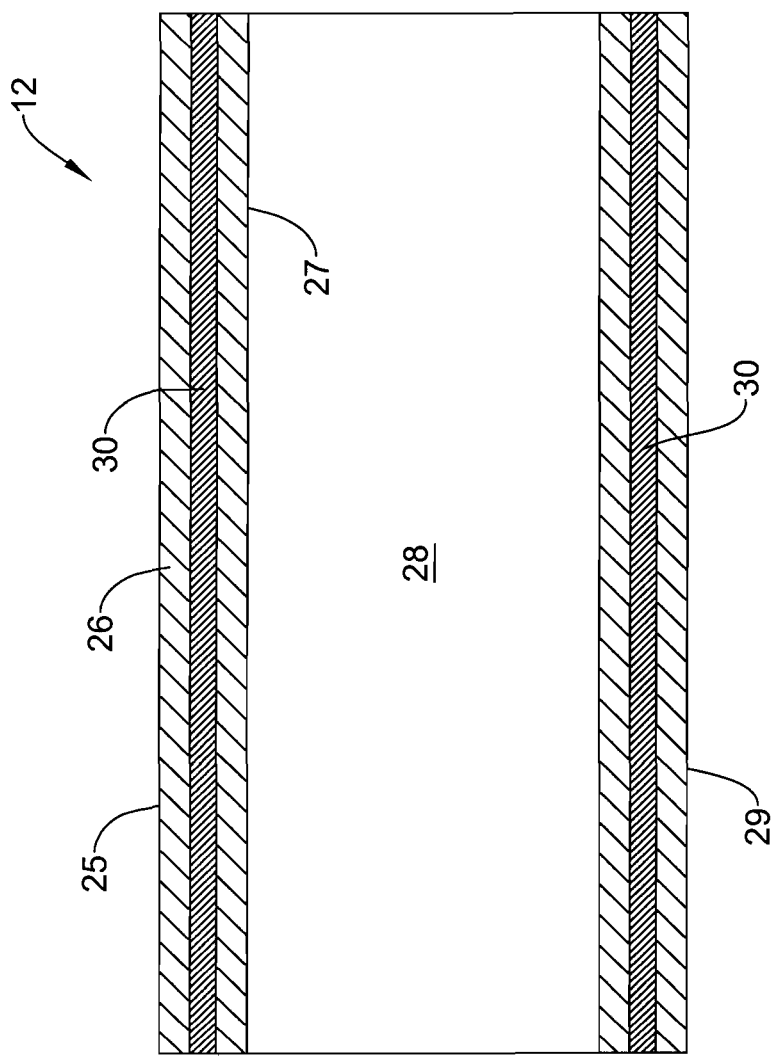
FIG. 3A is a cross-sectional view of a portion of the catheter shaft taken along line 3-3 of FIG. 1.

FIG. 3A is a longitudinal cross-sectional view of a portion of the elongate shaft 12 of the catheter 10 taken along line 3-3 of FIG. 1. As shown in FIG. 3A, in some embodiments the electrically conductive pathways, shown as electrically conductive wires 30, may longitudinally extend through the wall 25 of the tubular member 26. In other words, the electrically conductive wires 30 may extend generally parallel with the central longitudinal axis of the tubular member 26 in some embodiments. It is noted that although the electrically conductive pathways of the elongate shaft 12 shown in FIG. 3A are depicted as electrically conductive wires 30, one of skill in the art would understand that the electrically conductive pathways may be electrically conductive media 130 as described above, or other electrically conductive material.

Figure 3B:
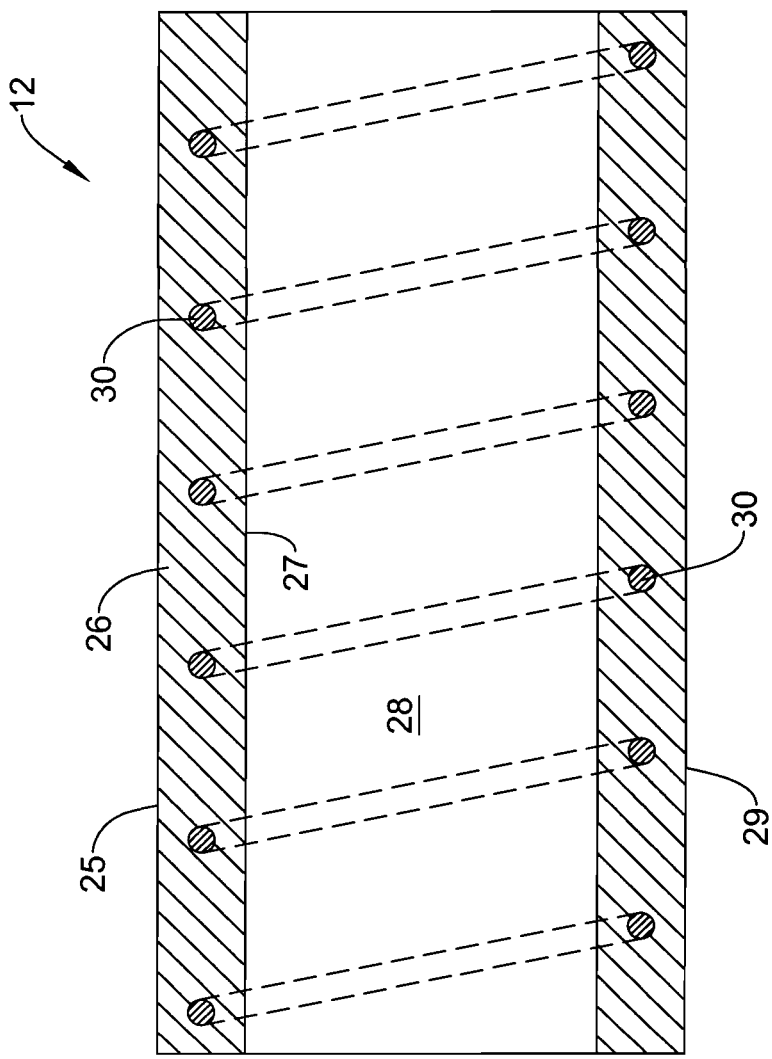
FIG. 3B is an alternative cross-sectional view of a portion of the catheter shaft taken along line 3-3 of FIG. 1.

FIG. 3B is an alternative longitudinal cross-sectional view of a portion of the elongate shaft 12 of the catheter 10 taken along line 3-3 of FIG. 1. As shown in FIG. 3B, in some embodiments the electrically conductive pathways, shown as electrically conductive wires 30, may helically extend along the length of the tubular member 26 embedded within the wall 26 of the tubular member 26. It is noted that although the electrically conductive pathways of the elongate shaft 12 shown in FIG. 3B are depicted as electrically conductive wires 30, one of skill in the art would understand that the electrically conductive pathways may be electrically conductive media 130 as described above, or other electrically conductive material.

Figure 4:
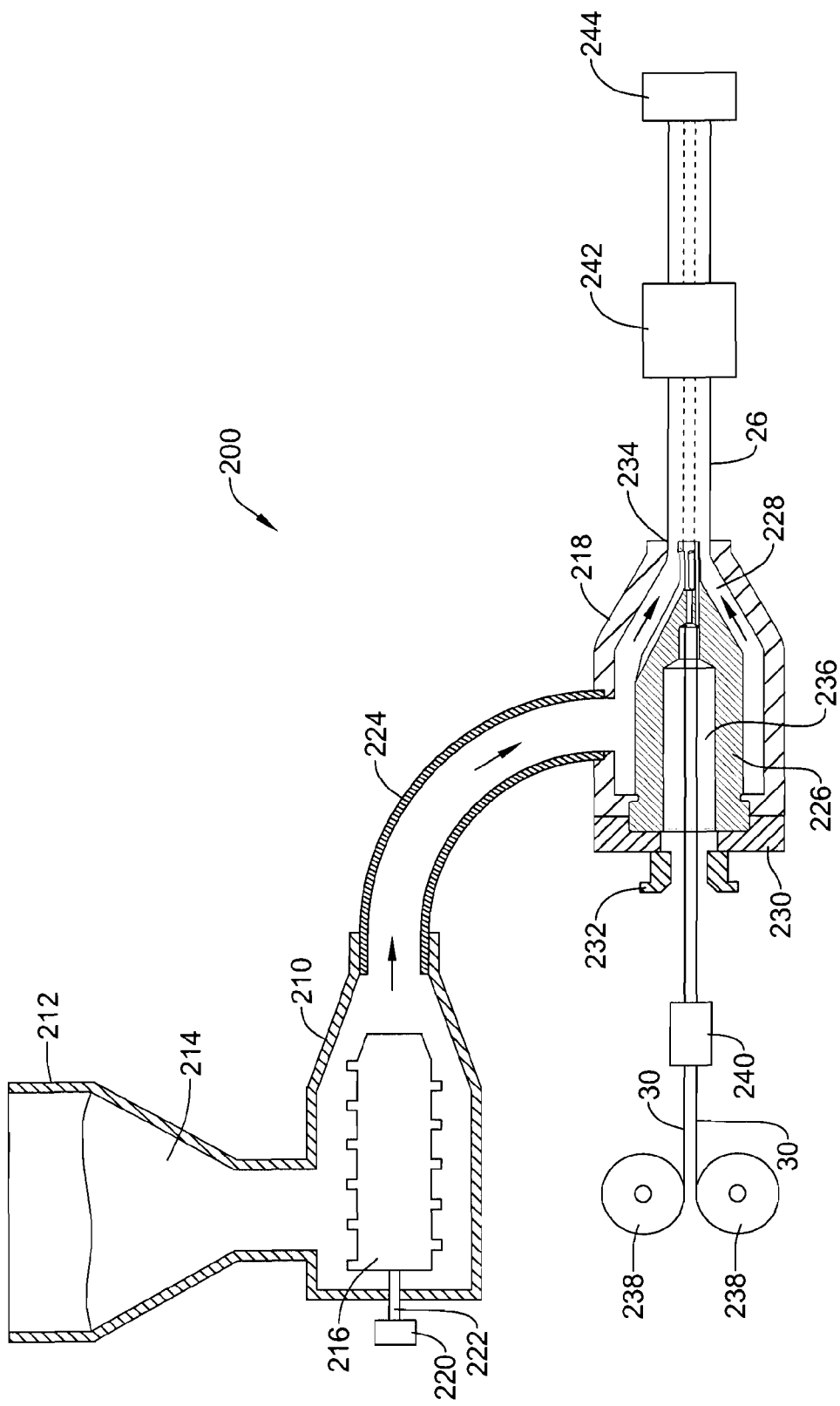
FIG. 4 illustrates an exemplary extrusion system.

FIG. 4 depicts an exemplary extrusion system 200 including an extruder 210 which may be used to form the tubular member 26 of the elongate shaft 12 of the catheter 10 shown in FIG. 1 during an extrusion process. The extruder 210 may include a hopper 212 containing a quantity of a polymeric material 214 for forming the tubular member 26. A screw 216 may deliver the polymeric material 214 through a conduit 224 to the extruder head 218. For example, a motor 220 may deliver rotational power through a shaft 222 to the screw 216 pushing polymeric material 214 toward the extruder head 218 through the conduit 224.

An extrusion die or mandrel 226 may be located within the extrusion head 218. In some embodiments, the extrusion die 226 may be heated to an elevated temperature during the extrusion process. The extrusion die 226 is shaped and configured to embed an electrically conductive material (e.g., electrically conductive wire or electrically conductive media) within the wall of a tubular member 26 extruded with the extrusion system 200. The extrusion die 226 may be housed within a cavity 228 of the extrusion head 218, leaving a gap between the extrusion die 226 and the extrusion head 218 for molten polymeric material to flow (as shown by arrows in FIG. 4). In some embodiments, the extrusion die 226 may be positioned in the extrusion head 218 such that the central longitudinal axis of the extrusion die 226 is longitudinally aligned with the central longitudinal axis of the extrusion head 218. In other words, the central longitudinal axis of the extrusion die 226 may be aligned with the center of the opening 234 of the extrusion head 218 in some embodiments. In some embodiments, the extrusion die 226 may be secured in the extrusion head 218 by securing an end cap 230 onto the rear of the extrusion head 218 with one or more fasteners, or the like. Further discussion of the extrusion die 226 will be provided while referring to FIGS. 5 and 5A-5B, herein.

Electrically conductive wires 30 may be fed into the central bore 236 of the extrusion die 226 through the rear of the extrusion die 226. The electrically conductive wires 30 may be provided on one or more spools 238, and thus unrolled off the spools 238 during an extrusion process. In some embodiments, rotational resistance of the spools 238 may cause tension to be placed on the electrically conductive wires 30. Thus, the tension of the wires 30 may be selectively controlled to achieve to proper tension of the wires 30 during the extrusion process. In some embodiments, a guide sleeve 232 may be present to help guide the electrically conductive wires 30 into the extrusion head 218.

In some embodiments, the electrically conductive wires 30 may be fed through a wire preheater 240 prior to being fed into the extrusion die 226. The wire preheater 240 may elevate the temperature of the electrically conductive wires 30 to a temperature above room temperature (e.g., greater than 22° C.). For example, in some embodiments, the wire preheater 240 may elevate the temperature of the electrically conductive wires 30 to a temperature above 50° C., above 75° C., above 100° C., above 125° C., above 150° C., or above 200° C. Heating the electrically conductive wires 30 may help increase the adherence of the polymeric tubing material around the electrically conductive wires 30 during the extrusion process.

After the extruded tubing 26 exits the extrusion head 218 through the opening 234 of the extrusion head 218, the tubing 26 may pass through a water bath 242, or other cooling apparatus. The water bath 242 may help cool the tubing 26 by extracting heat energy from the tubing 26 into water or other fluid by conduction. The extrusion system 200 may also include a puller 244 which controls the pull rate (i.e., longitudinal rate of advancement) of the tubing 26 out of the extrusion head 218.

During an extrusion process, the polymeric material 214 may be fed into the extrusion head 218 while one or more electrically conductive wires 30 are fed into the rear of the extrusion die 226 from the spools 238. As the polymer material 214 and electrically conductive wires 30 are passed through the extrusion head 218, the configuration of the extrusion die 226 allows for the polymeric material 214 to flow both radially interior of the wires 30 and radially exterior of the wires 30, such that the electrically conductive wires 30 are embedded within the wall of the tubing 26 upon exiting the opening 234 of the extrusion head 218. Thus, it can be seen that prior to exiting the opening 234 of the extrusion head 218, the electrically conductive wires 30 may be embedded within a single monolithic layer of polymeric material (i.e., a polymeric layer having a continuous molecular structure).

Figure 5:
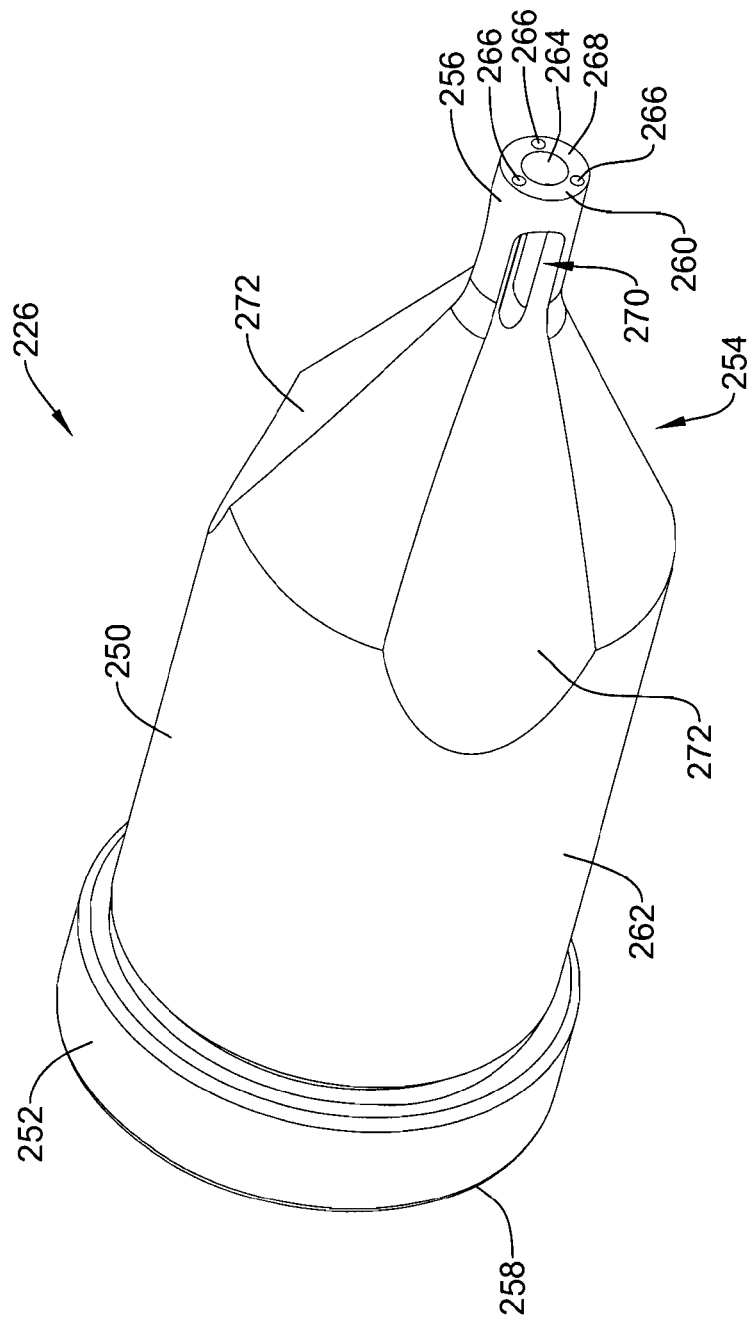
FIG. 5 is a perspective view of an illustrative extrusion die for use in the extrusion system of FIG. 4.

FIG. 5 is a perspective view of the extrusion die 226. The extrusion die 226 includes a body 250 including a generally cylindrical portion 262 and a base 252 at the rear end 258 of the body 250 of the extrusion die 226. The base 252 may have an enlarged diameter relative to the diameter of the cylindrical portion 262 of the body 250. The extrusion die 226 may also include a conical portion 254 forward of the cylindrical portion 262 and taper downward toward the forward end 260 of the body 250. As used herein, the use of the term "forward" when used to describe the extrusion die 226 is intended to refer to in the direction of extruded material leaving the extrusion head 218. As used herein, the use of the term "rear" when used to describe the extrusion die 226 is intended to refer to in the opposite direction of extruded material leaving the extrusion head 218.

The conical portion 254 of the body 250 may taper to a nose 256. In some embodiments, the nose 256 may be a generally cylindrical portion of the body 250 having an outer diameter less than the outer diameter of the cylindrical portion 262. The nose 256 may extend forward of the conical portion 254 to the forward end 260 of the extrusion die 226.

The nose 256 may include an annular wall 268 defining a central opening 264 extending therethrough which is in fluid communication with the central bore 236 of the body 250 of the extrusion die 226. The nose 256 may also include one or more wire lumens 266 extending within the annular wall 268 of the nose 256 to allow the passage of electrically conductive wires 30 therethrough. The nose 256, as shown in FIG. 5, includes three wire lumens 266 equally spaced radially around the annular wall 268 of the nose 256. However, in other embodiments, the nose 256 may include one, two, three, four, five, six or more wire lumens 266 equally spaced radially around the annular wall 268 or unequally spaced radially around the annular wall 268.

The nose 256 may also include one or more side openings 270 extending from the outer peripheral (e.g., circumferential) surface of the nose 256 inward through the annular wall 268 of the nose 256 to the central opening 264. The extrusion die 226 shown in FIG. 5 includes three side openings 270 extending radially inward through the annular wall 268 from exterior of the nose 256 to the central opening 264. However, in other embodiments, the nose 256 may include one, two, three, four, five, six, or more side openings 270. As shown in FIG. 5, the side openings 270 may be equally spaced radially around the annular wall 268 at a radial location opposite the radial location of the wire lumens 266. In other words, in some embodiments, the nose 256 may include a side opening 270 spaced about 180° opposite a wire lumen 266 of the nose 256. Thus, the side openings 270 may not interfere with the wire lumens 266. As will be explained later herein, the side openings 270 may allow polymeric material to enter the central opening 264 of the extrusion die 226 from radially exterior of the extrusion die 226.

The conical portion 254 of the extrusion die 226 may include one or more flutes 272 which may be radially aligned with the one or more side openings 270 of the nose 256. The extrusion die 226 includes three radially arranged flutes 272, however, in other embodiments the extrusion die 226 may include a different number of flutes 272, if desired. The flutes 272, which may be recessed into the otherwise conical shape of the conical portion 254, may further direct polymeric material toward and into the side openings 270 as well as around the exterior of the nose 256.

Figure 5A:
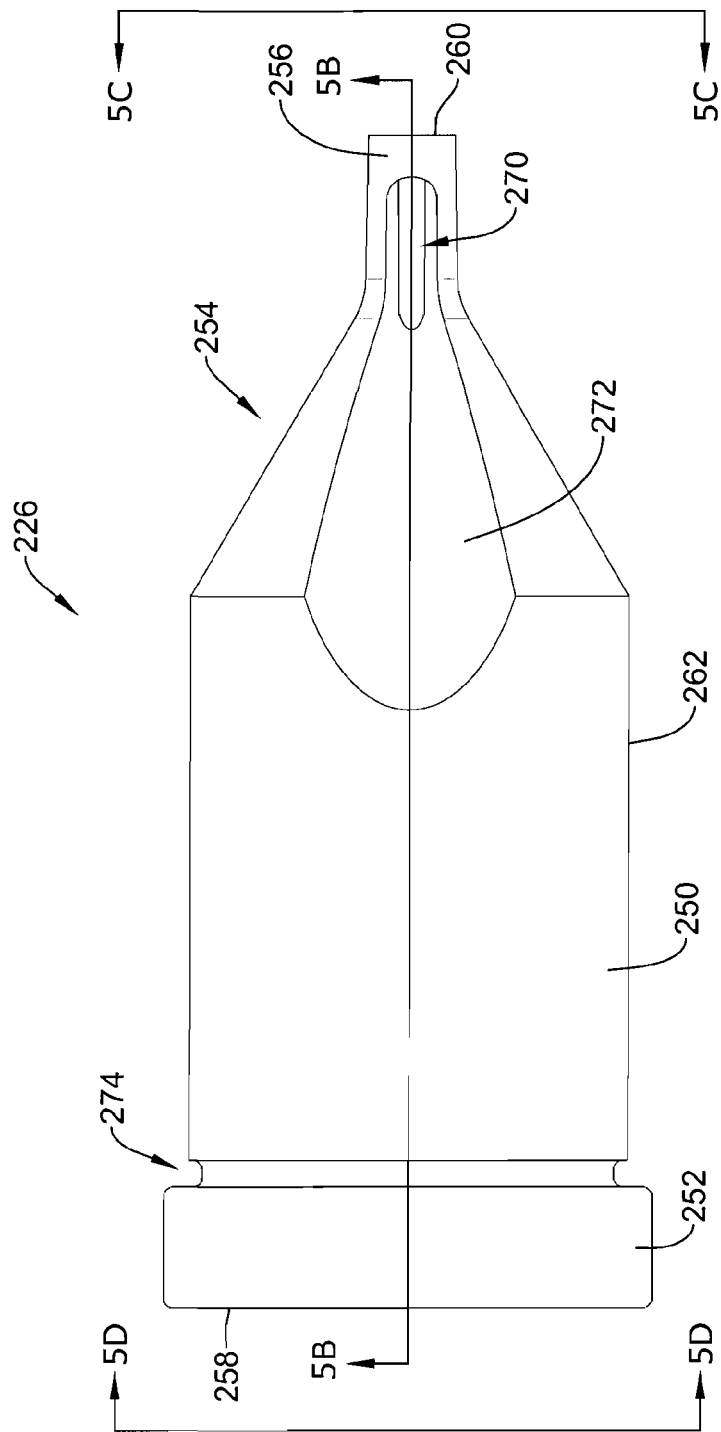
FIG. 5A is a side view of the extrusion die of FIG. 5.

FIGS. 5A through 5D further illustrate the extrusion die 226 shown in FIG. 5. FIG. 5A is a side view of the extrusion die 226. As shown in FIG. 5A, beginning at the rear end 258 of the extrusion die 226 and moving toward the forward end 260 of the extrusion die 226, the body 250 of the extrusion die 226 includes the base 252, followed by the cylindrical portion 262, followed by the conical portion 254, followed by the reduced diameter nose 256. A groove 274 may be present between the base 252 and the cylindrical portion 262 to further retain the extrusion die 226 within the extrusion head 218.

Figure 5B:
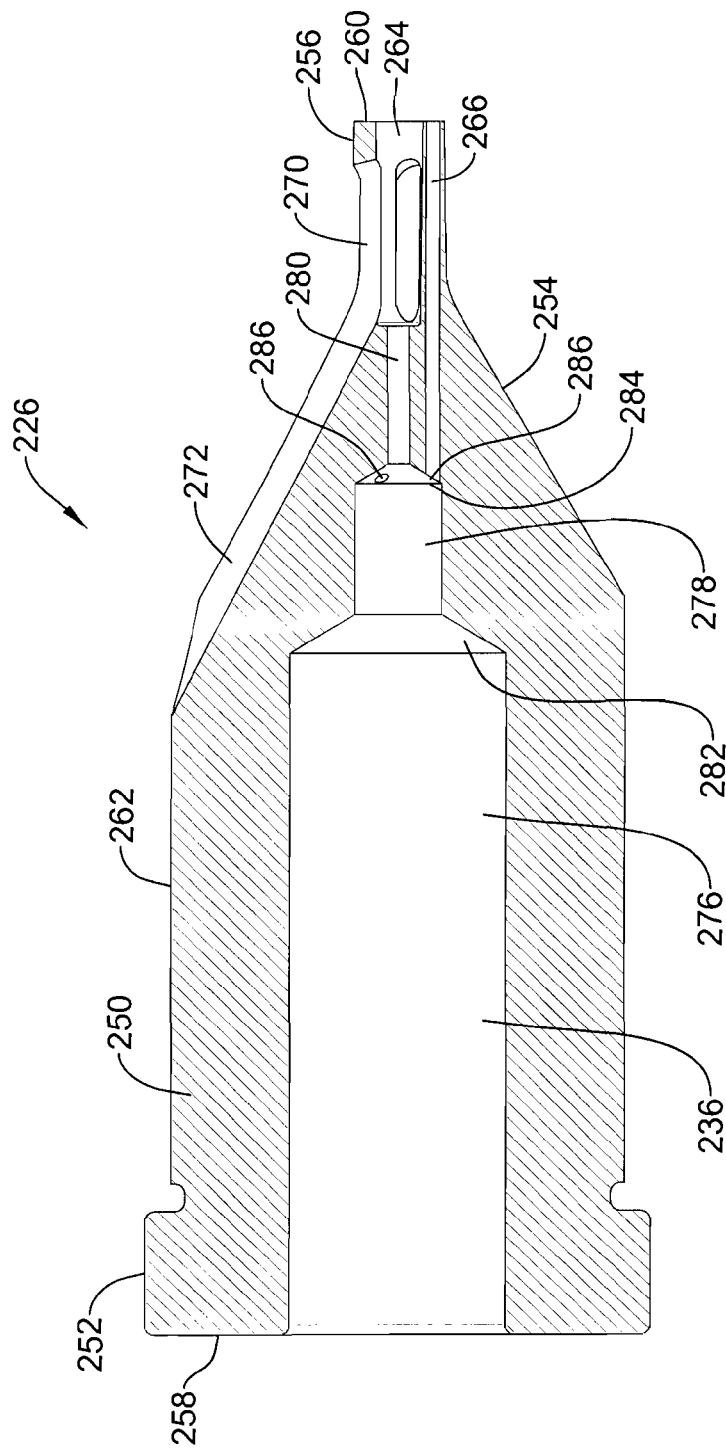
FIG. 5B is a longitudinal cross-sectional view of the extrusion die of FIG. 5 taken along line 5B-5B of FIG. 5A.

FIG. 5B is a cross-sectional view of the extrusion die 226 taken along line 5B-5B of FIG. 5A. As shown in FIG. 5B, the central bore 236 of the extrusion die 226, may include several sections of different diameters. For example, the central bore 236 may include a first cylindrical portion 276, a second cylindrical portion 278 and a third cylindrical portion 280. The first cylindrical portion 276 of the central bore 236 may have a first diameter, the second cylindrical portion 278 of the central bore 236 may have a second diameter less than the first diameter, and the third cylindrical portion 280 of the central bore 236 may have a third diameter less than the first diameter and the second diameter. At least a portion of the central bore 236 may have a diameter less than the diameter of the central opening 264 of the nose 256. For instance, the first cylindrical portion 276, the second cylindrical portion 278 and/or the third cylindrical portion 280 may have a diameter less than the diameter of the central opening 264 of the nose 256. The central bore 236 may also include a first tapered portion 282 between the first cylindrical portion 276 and the second cylindrical portion 278, and a second tapered portion 284 between the second cylindrical portion 278 and the third cylindrical portion 280.

As illustrated in FIG. 5B, the wire lumen 266 is shown extending from an opening 286 within the central bore 236 of the extrusion die 226 (e.g., at the second tapered portion 284), through the nose 256, to the forward end 260 of the extrusion die 226. Thus, it can be seen that an electrically conductive wire 30 may be inserted into the central bore 236 of the extrusion die 226 from the rear end 258. The electrically conductive wire 30 may then be inserted into the wire lumen 266 through the wire opening 286 at a location within the central bore 236. The electrically conductive wire 30 may then be extended through the wire lumen 266 to the forward end 260 of the extrusion die 226. Thus, it can be seen that an electrically conductive wire 30 passing through the extrusion die 226 may be located within the central bore 236 throughout a rearward portion of the extrusion die 226 and may be located within the wire lumen 266, and thus not be located within the central bore 236, throughout a forward portion of the extrusion die 226.

Additionally, as can be seen from FIG. 5B, during an extrusion process a mandrel may be inserted through the central bore 236 and into the central opening 264 of the nose 256 to maintain a central lumen in the polymeric tubing being extruded from the extrusion head 218. For instance, a mandrel having a diameter approximating the diameter of the third cylindrical portion 280 may be inserted through the central bore 236 to maintain a central lumen in the polymeric tubing.

Alternatively, pressurized fluid (e.g., air) may be supplied within the central bore 236 which will pass into the central opening 264 of the nose 256 radially interior of the polymeric material forming the polymeric tubing. The pressurized fluid may be used to maintain a central lumen in the polymeric tubing being extruded from the extrusion head 218.

Figure 5C:
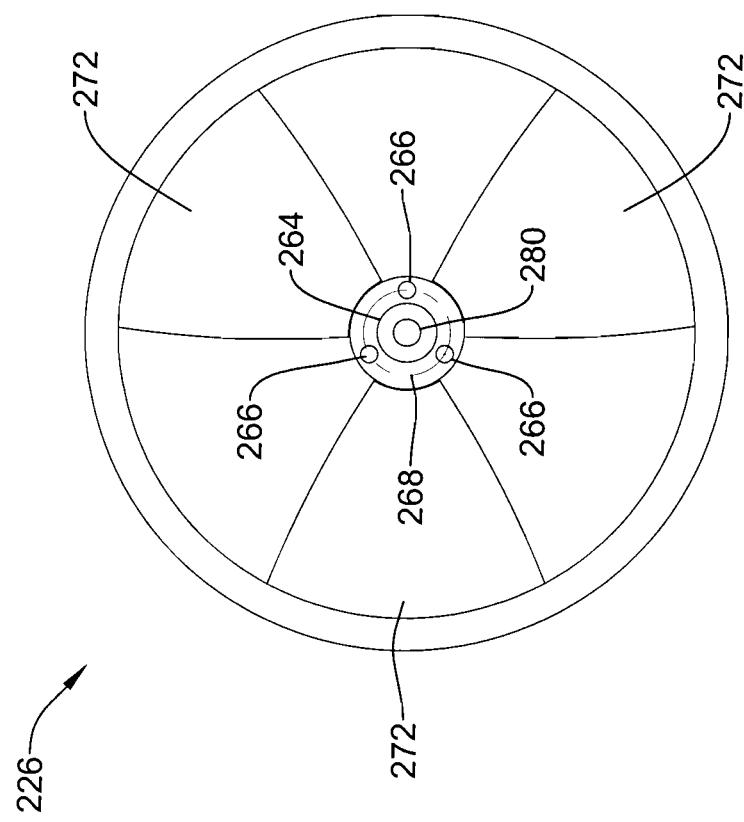
FIG. 5C is an end view of the extrusion die of FIG. 5 taken along line 5C-5C of FIG. 5A.

FIG. 5C is an end view of the extrusion die 226 taken along line 5C-5C of FIG. 5A of the forward end 260 of the extrusion die 226 in which the relationship of various portions of the extrusion die 226 may be further illustrated. As shown in FIG. 5C, the extrusion die 226 includes three wire lumens 266 radially arranged around the annular wall 268 of the nose 256. Additionally, a flute 272 may be located radially opposite each of the wire lumens 266. It is understood, however, that the extrusion die 226 may include any number of wire lumens 266 and/or flutes 272, as desired.

Furthermore, as shown in FIG. 5C, the third cylindrical portion 280 of the central bore 236 is shown centered within the central opening 264 of the nose 256. In other words, the central bore 236 of the extrusion die 226 and the central opening 264 of the nose 256 may share a common central longitudinal axis.

Figure 5D:
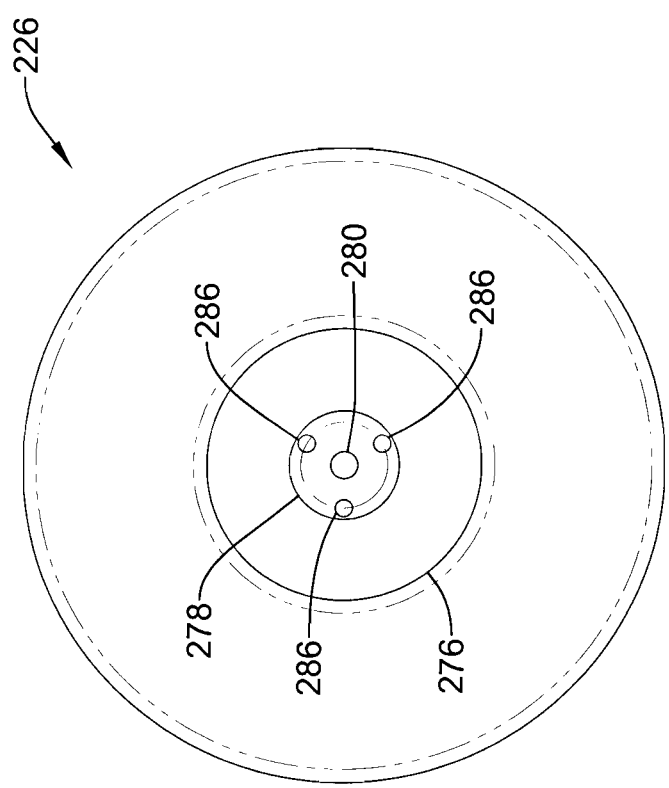
FIG. 5D is an end view of the extrusion die of FIG. 5 taken along line 5D-5D of FIG. 5A.

FIG. 5D is an end view of the extrusion die 226 taken along line 5D-5D of FIG. 5A of the rear end 258 of the extrusion die 226 in which the relationship of various portions of the extrusion die 226 may be further illustrated. As shown in FIG. 5D, the first cylindrical portion 276 of the central bore 236, the second cylindrical portion 278 of the central bore 236 and the third cylindrical portion 280 of the central bore 236 are illustrated as sharing a common central longitudinal axis.

Furthermore, as shown in FIG. 5D, the three wire openings 286 opening into the wire lumens 266 from the central bore 236 are shown radially arranged. As shown in FIG. 5D, the wire openings 286 may be radially arranged at a radial distance radially inward from the outer diameter of the second cylindrical portion 278 and radially outward from the outer diameter of the third cylindrical portion 280.

Figure 6:
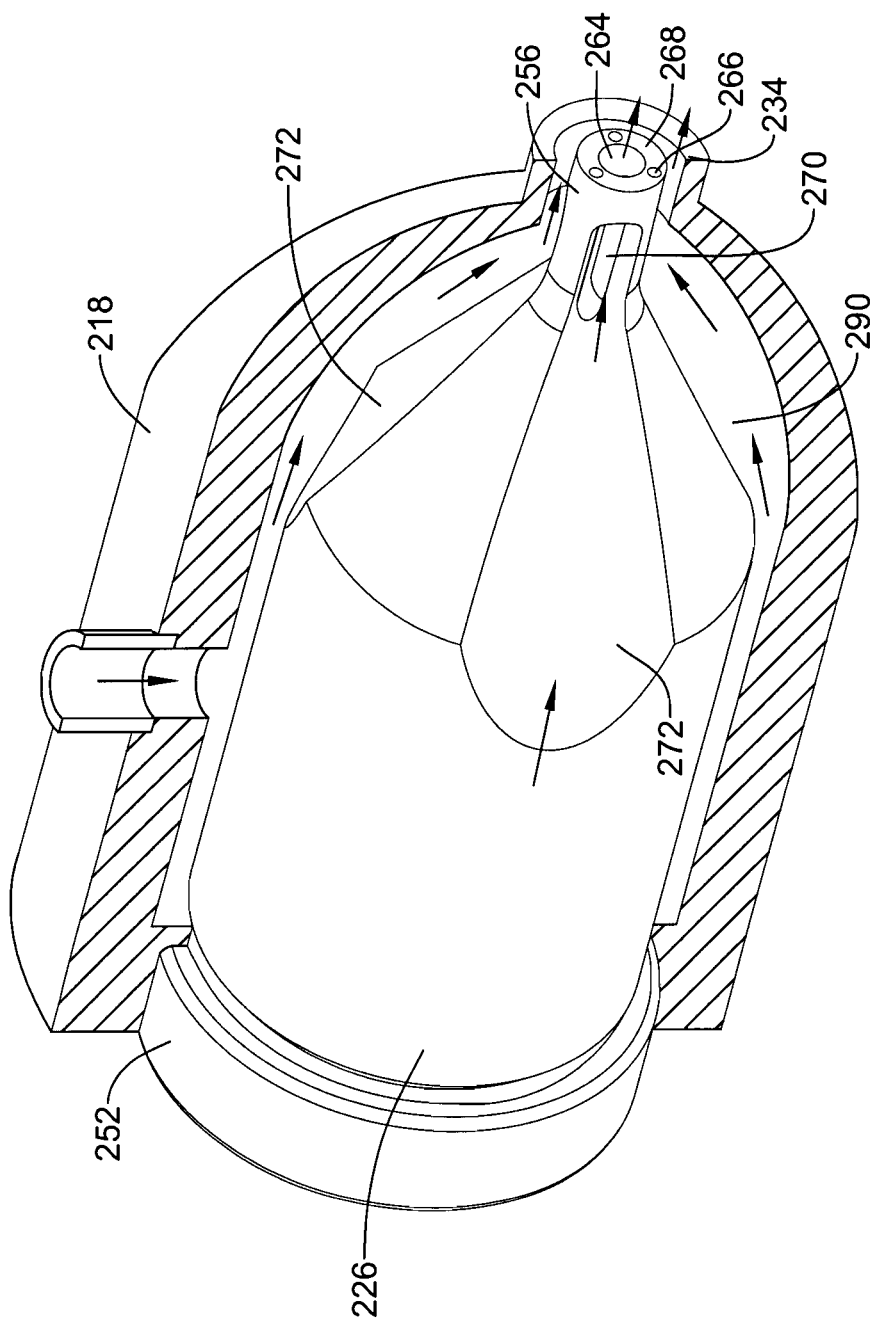
FIG. 6 is a perspective view of the extrusion die of FIG. 5 housed within a partially cut away extrusion head of an extrusion system during an extrusion process.

FIG. 6 is a perspective view of the extrusion die 226 positioned within the extrusion head 218, which has been partially cut away to better show the extrusion die 226. During an extrusion process, molten polymeric material (shown by arrows) may flow into the extrusion head 218 and around the extrusion die 226. The molten polymeric material may flow toward the opening 234 of the extrusion head 218 and occupies the space 290 between the extrusion die 226 and the extrusion head 218. As the molten polymeric material flows toward the opening 234, a portion of the molten polymeric material may be channeled by the flutes 272 into the side openings 270 of the nose 256 of the extrusion die 226, and into the central opening 264 of the nose 256. In other words, the extrusion die 226 may be configured to allow molten polymeric material to enter the central opening 264 of the nose 256 of the extrusion die 226 through the side openings 270. Thus, it can be seen from FIG. 6, as molten polymeric material flows toward the opening 234 of the extrusion head 218, molten polymeric material may flow both around the outer circumference of the nose 256 and within the central opening 264 of the nose 256. Therefore, as polymeric material is being extruded through extrusion head 218, polymeric material may be located both radially inward of the annular wall 268 of the nose 256 and radially outward of the annular wall 268 of the nose 256. Therefore, as the polymeric material exits the opening 234 of the extrusion head 218, there may be polymeric material located between the inner surface of the extrusion head 218 and the outer surface of the nose 256 of the extrusion die 226 and polymeric material located in the central opening 264 of the nose 256 of the extrusion die 226.

As described above, during an extrusion process a mandrel may be inserted through the central bore 236 and into the central opening 264 of the nose 256 to maintain a central lumen in the polymeric material being extruded from the extrusion head 218. Alternatively, pressurized fluid (e.g., air) may be supplied within the central bore 236 which will pass into the central opening 264 of the nose 256 radially interior of the polymeric material forming the polymeric tubing in order to maintain a central lumen in the polymeric material being extruded from the extrusion head 218.

As can be seen from FIG. 6, electrically conductive wires 30 being drawn through the wire lumens 266 of the extrusion die 226 may be encased within the polymeric material exiting the extrusion head 218. In other words, the portion of the polymeric material passing through the central opening 264 of the nose 256 of the extrusion die 226 may be located radially inward of the electrically conductive wires 30 being drawn through the wire lumens 266, and the portion of the polymeric material passing radially outward of the outer circumferential surface of the nose 256 of the extrusion die 226 may be located radially outward of the electrically conductive wires 30 being drawn through the wire lumens 266. Thus, as the electrically conductive wires 30 are drawn out of the opening 234 of the extrusion head 218, extruded polymeric material may be located both radially inward of the electrically conductive wires 30 and radially outward of the electrically conductive wires 30 of the polymeric tubing formed during the extrusion process. Thus, the electrically conductive wires 30 may be drawn through the extrusion head 218 as the polymeric material is being extruded from the extrusion head 218 to embed the electrically conductive wires 30 within the annular wall of a polymeric tubing formed during the extrusion process. In the disclosed extrusion system and method, the electrically conductive wires 30, which are drawn through the extrusion die 226, first contact the polymeric material forward of the forward end 260 of the extrusion die 226, at which point polymeric material encapsulates, or surrounds, the electrically conductive wires 30.

Figure 7C:
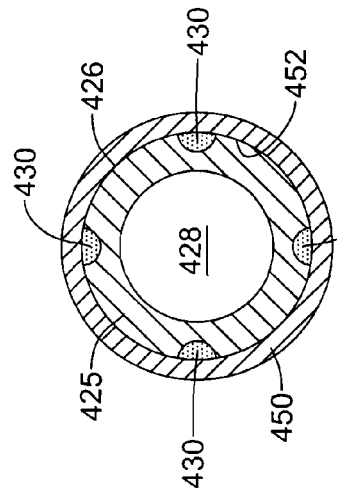
FIGS. 7A-7C illustrate an exemplary method of providing an electrically conductive pathway through an elongate tubular member.
Figure 7A:
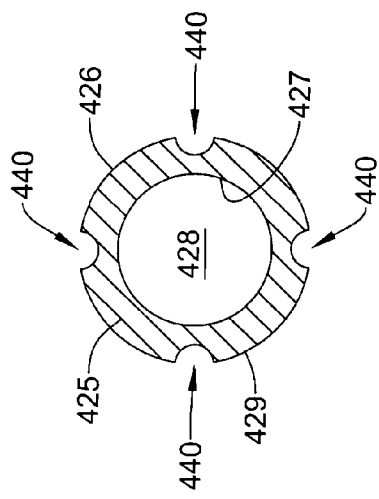
Figure 7B:
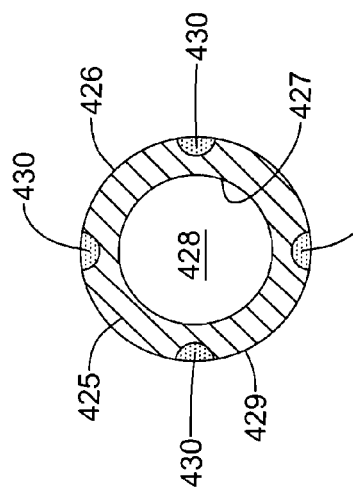

FIGS. 7A through 7C illustrate another method of incorporating an electrically conductive pathway through an elongate shaft of a catheter. As shown in FIG. 7A, a tubular member 426 may be extruded during an extrusion process. The tubular member 426 may include a wall 425 having an outer surface 429 and an inner surface 427 defining a lumen 428 extending through the tubular member 426. Through the extrusion process, the wall 425 of the tubular member 426 may be extruded to include one or more, or a plurality of recesses 440, such as longitudinal recesses extending longitudinally along the length of the tubular member 426. For example, the tubular member 426 may have an outer surface 429 defining an outer diameter of the tubular member 426, and the recesses 440 may extend radially inward from the outer diameter of the tubular member 426. Thus, the radial thickness of the wall 425 of the tubular member 426 may be less at the radial location of the recesses 440 than the radial thickness of the wall 425 of the tubular member 426 at other radial locations of the tubular member 426.

As shown in FIG. 7B, the recesses 440 may be filled, such as during a simultaneous or subsequent extrusion process, with an electrically conductive media 430. For example, the recesses 440 may be filled with an electrically conductive media 430 such that the void space of recesses 440 in the wall 425 of the tubular member 426 is entirely filled, substantially filled, partially filled, or otherwise occupied by a quantity of electrically conductive media 430. In some embodiments, the electrically conductive media 430 may fill the void space of the recesses 440 in the wall 425 such that the radial outer extent of the electrically conductive media 430 is even with the outer extent of the outer surface 429 of the tubular member 426. In other embodiments, the radial outer extent of the electrically conductive media 430 may be radially outward from the outer extent of the outer surface 429 of the tubular member 426, or the radial outer extent of the electrically conductive media 430 may be radially inward from the outer extent of the outer surface 429 of the tubular member 426.

The electrically conductive media 430 may be similar to the electrically conductive media 130 described above. For example the electrically conductive media 430 may be any desired media which is electrically conductive. In some embodiments, the electrically conductive media 430 may be a conductive ink, a conductive powder, a conductive paste, a conductive epoxy, a conductive adhesive, a conductive polymer or polymeric material, or other conductive material. For example, the electrically conductive media 430 may include about 0.5% to about 40%, about 1% to about 30%, or about 10% to about 30% by weight of metallic particles suspended in a generally non-conductive medium. For instance, in some embodiments, the electrically conductive media 430 may include silver, gold, platinum, carbon, stainless steel, or magnesium particles suspended in a generally non-conductive medium. In some embodiments, the non-conductive medium may be a polymeric material, a ceramic material, an ink, an epoxy, an adhesive, or other desired material. The presence of the electrically conductive particles in the generally non-conductive medium may provide the electrically conductive media 430 with adequate conductivity to pass an electrical current along the electrically conductive media 430.

In some embodiments, the electrically conductive media 430 may be disposed in the recesses 440 of the tubular member 426 while the electrically conductive media 430 is in a liquid state, a gel state, or a sol state, such that the electrically conductive media 430 has a volume which takes the shape of that which it is in contact with, and then the electrically conductive media 430 may harden into a solid state after being disposed in the recesses 440. For example, after being disposed in the recesses 440, the electrically conductive media 430 may be cured and/or cooled to transition to a solid state.

As shown in FIG. 7C, with the recesses 440 filled with an electrically conductive media 430, an outer layer 450 may be disposed over the tubular member 426. For example, the outer layer 450 may be disposed over the tubular member 426 such that the inner surface 452 of the outer layer 450 may be in contact with the outer surface 429 of the tubular member 426. In some embodiments, the inner surface 452 of the outer layer 450 may be in contact with the electrically conductive media 430.

In some embodiments, the outer layer 450 may be extruded over the tubular member 426 subsequent to disposing the electrically conductive media 430 in the recesses 440 of the tubular member 426. In some embodiments, the outer layer 450 may be a length of heat shrink tubing disposed over the tubular member 426 and then exposed to heat in order to shrink the heat shrink tubing around the outer surface 429 of the tubular member 426. With the outer layer 450 disposed on the tubular member 426, the electrically conductive media 430 may be bounded by the tubular member 426 and the outer layer 450.

Although the recesses 440 of the tubular member 426 are shown extending inward from the outer surface 429 of the wall 425 of the tubular member 426, in other embodiments, the tubular member 426 may include one or more, or a plurality of recesses extending radially outward from the inner surface 427 of the wall 425 of the tubular member 426. The recesses may be occupied by electrically conductive media 430. In such embodiments, an inner layer may be disposed within the lumen 428 of the tubular member 426 and in contact with the inner surface 427 of the wall 425 of the tubular member 426, such that the electrically conductive media 430 is bounded by the tubular member 426 and the inner layer.

Figure 8:
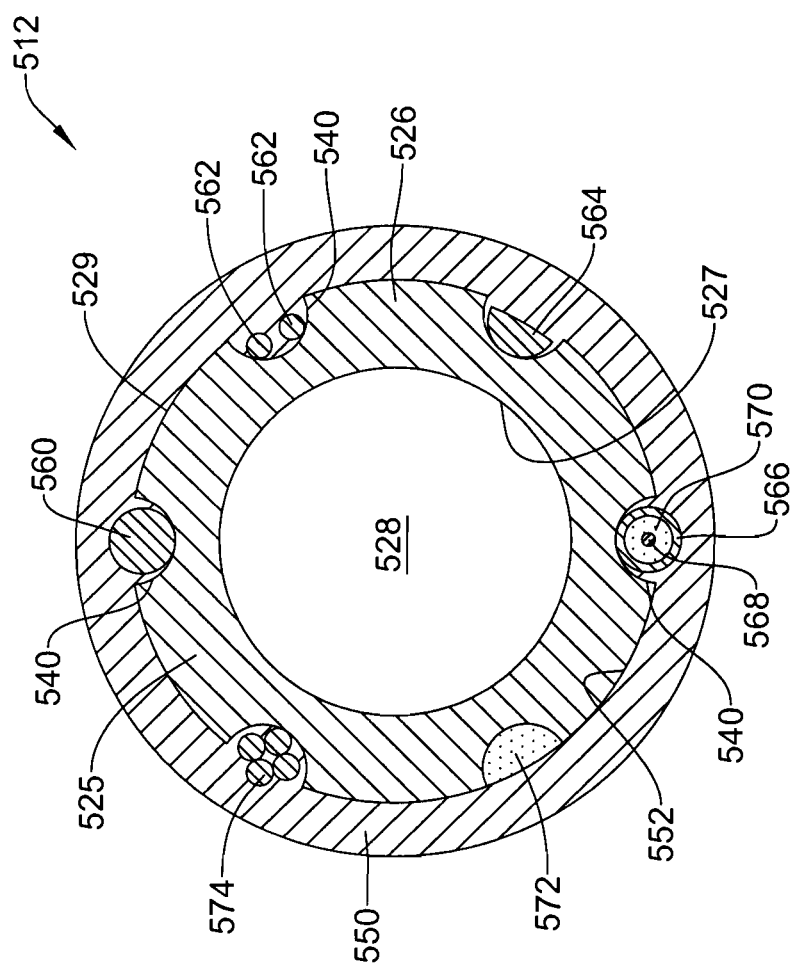
FIG. 8 illustrates several alternative configurations of an elongate shaft of a catheter which includes one or more, or a plurality of electrically conductive pathways extending along a length of the elongate shaft.

FIG. 8 illustrates several alternative configurations of an elongate shaft 512 of a catheter which includes one or more, or a plurality of electrically conductive pathways extending along a length of the elongate shaft 512. Although several alternative electrically conductive pathways are illustrated in a single elongate shaft, one of skill in the art would understand that a catheter shaft may include one or more of the several illustrated electrically conductive pathways of FIG. 8. Any of the disclosed electrically conductive pathways may be formed of electrically conductive materials as described elsewhere throughout this disclosure.

The elongate shaft 512 may include a tubular member 526. The tubular member 526 may include a wall 525 having an outer surface 529 and an inner surface 527 defining a lumen 528 extending through the tubular member 526. In some embodiments, the tubular member 526 may be formed during an extrusion process. Through the extrusion process, the wall 525 of the tubular member 526 may be extruded to include one or more, or a plurality of recesses 540, such as longitudinal recesses extending longitudinally along the length of the tubular member 426. For example, the tubular member 526 may have an outer surface 529 defining an outer diameter of the tubular member 526, and the recesses 540 may extend radially inward from the outer diameter of the tubular member 526. Thus, the radial thickness of the wall 525 of the tubular member 526 may be less at the radial location of the recesses 540 than the radial thickness of the wall 525 of the tubular member 526 at other radial locations of the tubular member 526.

One exemplary electrically conductive pathway is shown as an electrically conductive wire 560 located in a longitudinal recess 540 of the tubular member 526. Another electrically conductive pathway is shown as a pair of electrically conductive wires 562 located within a single longitudinal recess 540 of the tubular member 526. In such an embodiment, one of the pair of electrically conductive wires 562 may pass an electrical current distally along the tubular member 526, and the other of the pair of electrically conductive wires 562 may pass an electrical current back proximally along the tubular member 526. The first of the pair of electrically conductive wires 562 may be spaced from the second of the pair of electrically conductive wires 562 to prevent an electrical short across the wires 562. The outer layer 550 may maintain separation between the pair of electrically conductive wires 562.

Another exemplary electrically conductive pathway is shown as an electrically conductive piezoelectric material, such as a piezoelectric ceramic material. The piezoelectric material may provide an electrically conductive pathway along the tubular member 526. Yet another exemplary electrically conductive pathway is shown as a metallic tube 566, such as a hypotube, surrounding a core wire 568. An insulative layer 570 may be positioned between the core wire 568 and the metallic tube 566 to prevent an electrical short across the wire 568 and tube 566. One of the core wire 568 and the metallic tube 566 may pass an electrical current distally along the tubular member 526, and the other of the core wire 568 and the metallic tube 566 may pass an electrical current proximally along the tubular member 526.

A further exemplary electrically conductive pathway is shown as an electrically conductive media 572, similar to the electrically conductive media 130 described above. Yet another electrically conductive pathway is shown as an electrically conductive wire braid 574 including a plurality of wires braided together. In some embodiments, one or more of the wires of the wire braid 574 may be formed of an electrically conductive material (e.g., metallic) and one or more of the wires of the wire braid 574 may be formed of an electrically insulative material (e.g., polymeric). The wire braid 574 may be located within a recess 540 of the tubular member 526. Providing a wire braid 574 may provide a greater amount of surface area for an electrical current to travel along within the same space as a single, larger wire having the same diameter as the diameter of the wire braid 574.

As shown in FIG. 8, with one or more electrically conductive pathways occupying the recesses 540, an outer layer 550 may be disposed over the tubular member 526. For example, the outer layer 550 may be disposed over the tubular member 526 such that the inner surface 552 of the outer layer 550 may be in contact with the outer surface 529 of the tubular member 526. In some embodiments, the inner surface 552 of the outer layer 550 may be in contact with the electrically conductive pathways.

In some embodiments, the outer layer 550 may be extruded over the tubular member 526 subsequent to disposing the electrically conductive pathways in the recesses 540 of the tubular member 526. In some embodiments, the outer layer 550 may be a length of heat shrink tubing disposed over the tubular member 526 and then exposed to heat in order to shrink the heat shrink tubing around the outer surface 529 of the tubular member 526. With the outer layer 550 disposed on the tubular member 526, the electrically conductive pathways may be bounded by the tubular member 526 and the outer layer 550.

Figure 9:
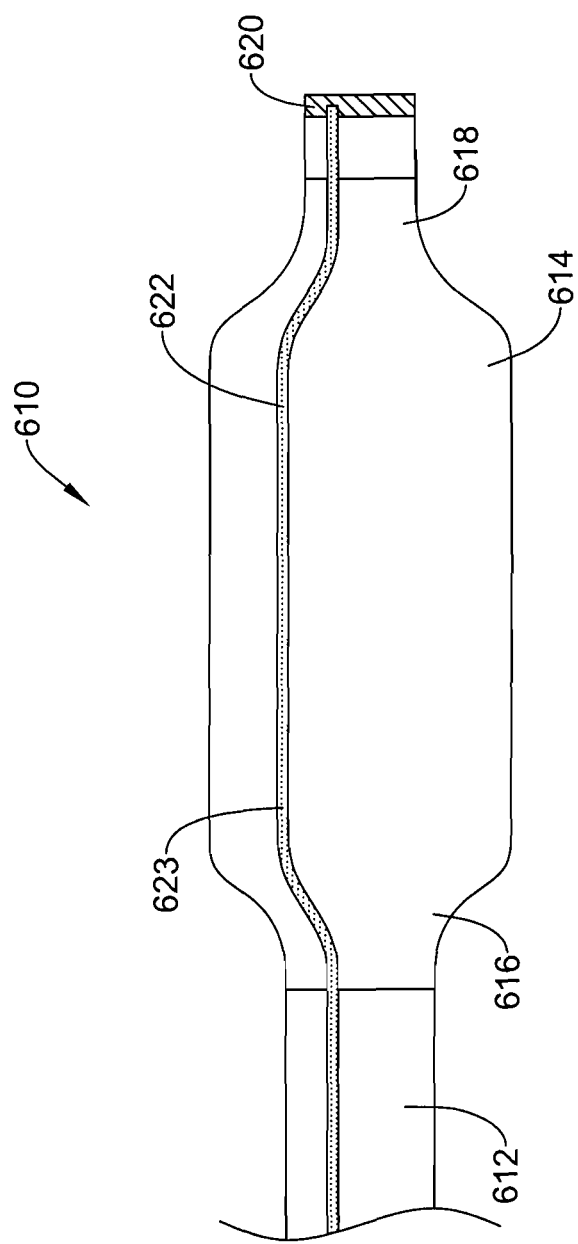
FIG. 9 depicts a distal portion of a balloon catheter including an electrically conductive pathway.

A distal portion of a balloon catheter 610 is shown in FIG. 9. The balloon catheter 610 includes an elongate shaft 612 and an inflation balloon 614 secured to the elongate shaft 612. For example, a proximal waist 616 of the balloon 614 may be secured (e.g., adhesively bonded or thermally bonded) to the elongate shaft 612 and a distal waist 618 of the balloon 614 may be secured (e.g., adhesively bonded or thermally bonded) to the elongate shaft 612.

The catheter 610 may include a working element 620 located, for example, distal of the balloon 614 near the distal end of the catheter shaft 612. The working element 620 may utilize electrical current during operation. For example the working element 620 may be an electrical cauterization device, an electrolysis device, an electrolysis controlled drug eluting balloon and/or stent, electrodes, a thermal ablation device, a radio frequency device, an ultrasonic device (e.g., ultrasonic transducer), an electroportation device, a device incorporating electro-active polymer (EAP), NG detachable coils, a brachy therapy radiation device, a micro-perfusion pump, an infrared device, an atherectomy device, an electro-active neurovascular coil, a sensor such as a temperature, flow, force, strain, or pressure sensor, or other working element utilizing an electrical current to perform a medical procedure or treatment within a patient's body.

The catheter 610 may include an electrically conductive pathway 622 extending along the exterior of the catheter shaft 612 and/or the balloon 614 from a proximal portion of the catheter 610 to the working element 620. For example, the electrically conductive pathway 622 may be an electrically conductive ink 623 bonded (e.g., cured) to the exterior of the catheter shaft 612 and/or the balloon 614. Some possible electrically conductive inks include an electrically conductive silver ink, an electrically conductive carbon ink, or an electrical conductive gold ink. Some suitable electrically conductive inks are sold by Creative Materials of Tyngsboro, Mass. In some embodiments, the electrically conductive ink 623 may include or be mixed with an adhesive, epoxy, or other material to facilitate bonding the ink to the catheter shaft 612 and/or the balloon 614.

The electrically conductive ink 623 may be printed, or otherwise applied, onto the exterior of the catheter shaft 612 and/or the balloon 614. For example, the electrically conductive ink 623 may be screen printed or pad printed onto the catheter shaft 612 and/or the balloon 614.

Figure 10A:
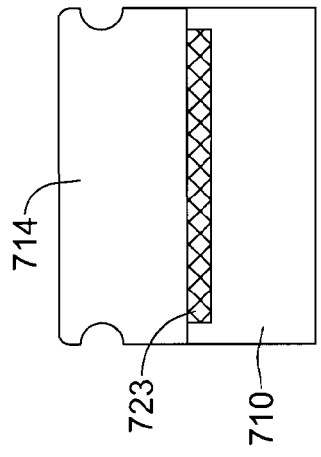
FIGS. 10A-10F illustrate an exemplary pad printing process for applying an electrically conductive pathway to a medical device.
Figure 10B:
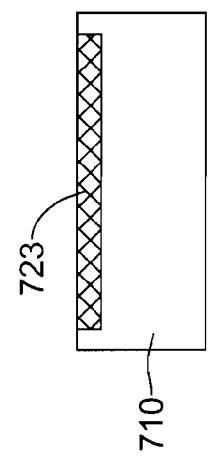
Figure 10C:
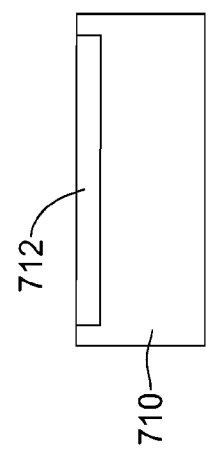
Figure 10D:
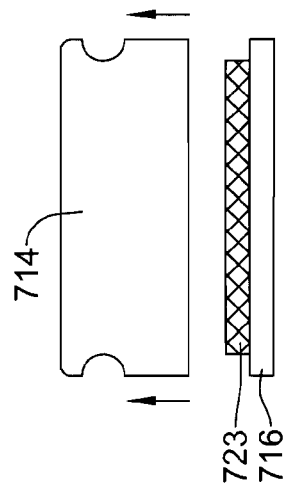
Figure 10E:
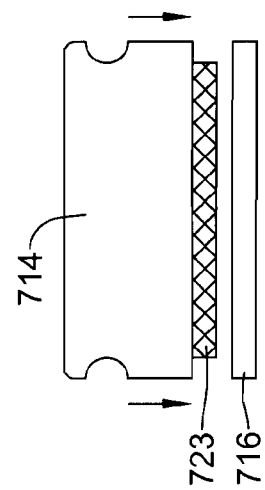
Figure 10F:
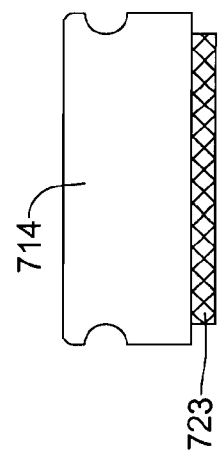

Referring to FIGS. 10A through 10F, an exemplary pad printing process is schematically illustrated. As shown in FIG. 10A, in embodiments utilizing a pad printing process, a stereotype plate (i.e., a print plate, cliché) 710 may be provided with a channel or reservoir 712. The reservoir 712 of the stereotype plate 710 may be filled with an electrically conductive ink 723, as shown in FIG. 10B. A pad 714, shown in FIG. 10C, may then be positioned over the stereotype plate 710 and pressed onto the stereotype plate 710 into contact with the electrically conductive ink 723. In some embodiments, the pad 714 may be formed of a urethane material or silicone material. The electrically conductive ink 723 is picked up by the pad 714, as shown in FIG. 10D, and thus, removed from the reservoir 712 of the stereotype plate 710 by the pad 714. The electrically conductive ink 723 has sufficient adhesion to the pad 714 to maintain adherence to the pad 714 prior to being applied to a substrate. As shown in FIG. 10E, with the electrically conductive ink 723 on the pad 714, the pad 714 is brought into contact with the desired substrate 716 (e.g., catheter shaft, catheter balloon, etc.). The pad 714 is pressed down on the substrate 716, depositing the electrically conductive ink 723 onto the substrate 716. The affinity of the electrically conductive ink 723 to bond with the substrate 716 is greater than the electrically conductive ink's affinity to bond to the pad 714, thus allowing the electrically conductive ink 723 to be transferred to the substrate 716. The pad 714 may then be lifted away from the substrate 716, leaving the electrically conductive ink 723 on the substrate 716. Thus it can be seen that the pad 714 transfers the electrically conductive ink 723 to the substrate 716. This process may be repeated, as desired, to create a pathway of an electrically conductive ink of any desired length or arrangement.

Figure 11:
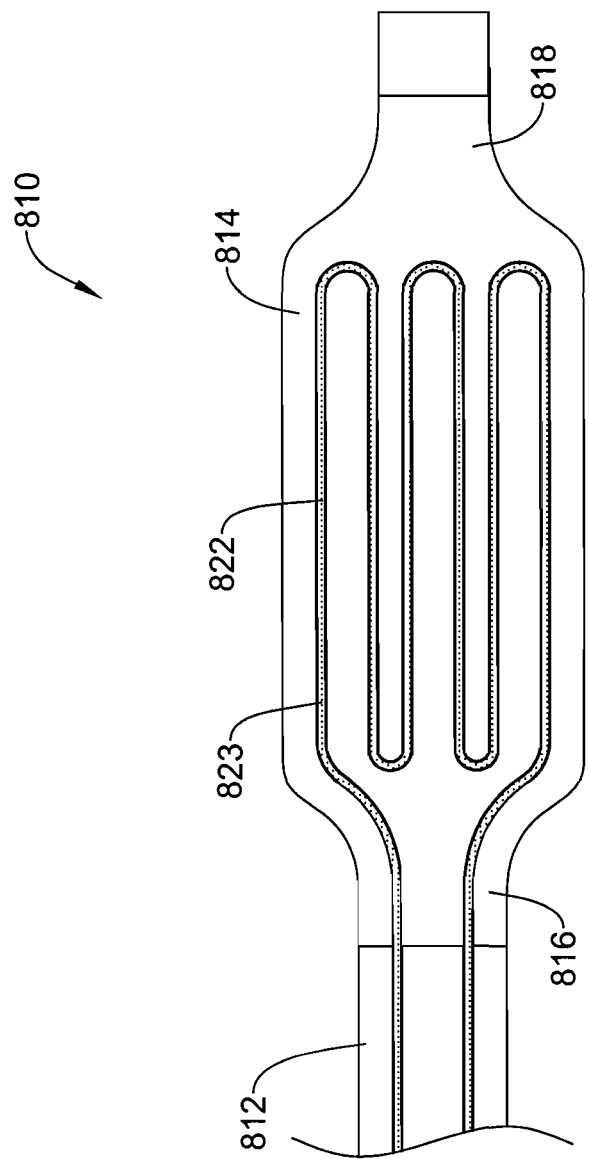
FIG. 11 depicts a distal portion of a balloon catheter including an electrically conductive pathway.

A distal portion of another balloon catheter 810 is shown in FIG. 11. The balloon catheter 810 includes an elongate shaft 812 and an inflation balloon 814 secured to the elongate shaft 812. For example, a proximal waist 816 of the balloon 814 may be secured (e.g., adhesively bonded or thermally bonded) to the elongate shaft 812 and a distal waist 818 of the balloon 814 may be secured (e.g., adhesively bonded or thermally bonded) to the elongate shaft 812.

The catheter 810 may include an electrically conductive pathway 822 extending along the exterior of the catheter shaft 812 and/or the balloon 814 from a proximal portion of the catheter 810 to the balloon 814. For example, the electrically conductive pathway 822 may be an electrically conductive ink 823 bonded (e.g., cured) to the exterior of the catheter shaft 812 and/or the balloon 814. In some embodiments, the electrically conductive ink 823 may be a pressure variable resistor ink. A pressure variable resistor ink is an electrically conductive ink which experiences a change in electrical resistance as pressure on the ink 823 changes. For example, in some embodiments, the electrically conductive ink 823 may experience a decrease in electrical resistance as pressure is increased. Some suitable pressure variable resistor inks are sold by Creative Materials of Tyngsboro, Mass. In some embodiments, the pressure variable resistor ink may include or be mixed with an adhesive, epoxy, or other material to facilitate bonding the ink to the catheter shaft 812 and/or the balloon 814.

The electrically conductive ink 823 may be printed, or otherwise applied, onto the exterior of the catheter shaft 812 and/or the balloon 814. For example, the electrically conductive ink 823 may be screen printed or pad printed onto the catheter shaft 812 and/or the balloon 814, as described above.

As shown in FIG. 11, the catheter shaft 812 may include a first pathway of electrically conductive ink 823 extending longitudinally along the exterior surface of the catheter shaft 812 from a proximal portion of the catheter shaft 812 to a distal portion of the catheter shaft 812. The catheter shaft 812 may also include a second pathway of electrically conductive ink 823 extending longitudinally along the exterior surface of the catheter shaft 812 from a proximal portion of the catheter shaft 812 to a distal portion of the catheter shaft 812.

The balloon 814 may include a serpentine pathway of the electrically conductive ink 823 deposited on an exterior surface of the balloon 814. For instance, the electrically conductive ink 823 may be deposited on the exterior surface of the balloon 814 in a back-and-forth, winding arrangement covering at least a portion of the exterior surface of the balloon 814.

The pressure variable resistor ink 823 may be used to indicate the pressure applied to a vessel or lumen wall when the balloon 814 is inflated within a patient's vessel or lumen. For instance, during an angioplasty procedure, a balloon of a balloon catheter may be inflated to press against a lesion or other treatment site within a patient's blood vessel. As shown in FIG. 11, a balloon 814 of a balloon catheter 810 provided with a pressure variable resistor ink 823 pathway may be able to provide feedback to an operator concerning what pressure is being experienced at the interface between the balloon 814 and the interior surface of the blood vessel. As the pressure experienced at the interface increases or decreases, the electrical resistance through the electrically conductive ink pathway 823 will be altered. The operator, utilizing an instrument exterior of the patient, may measure the electrical resistance value and/or change in electrical resistance passed through the electrically conductive ink 823 to determine the pressure experienced at the interface between the balloon 814 and the vessel wall.

Figure 12:
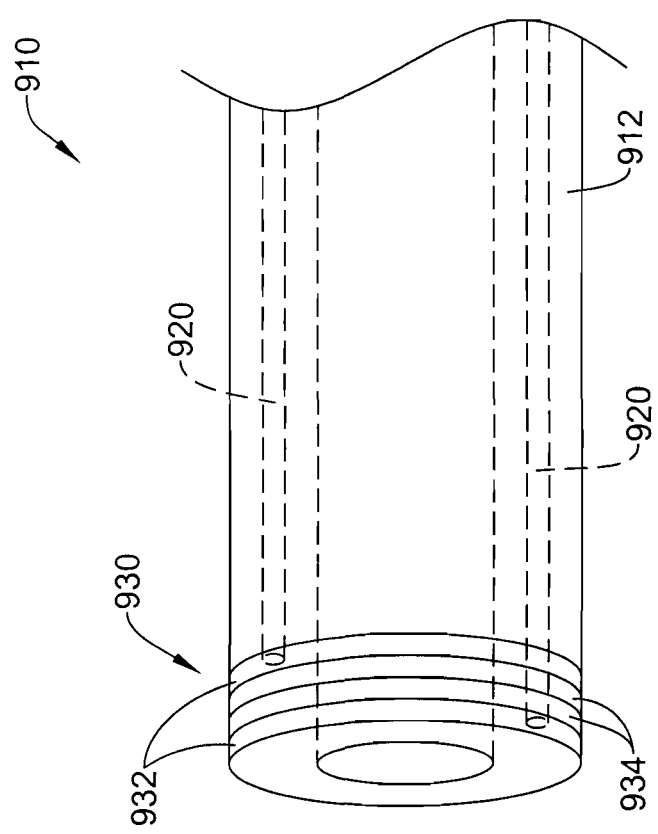
FIG. 12 depicts a distal portion of a catheter including an electrically sensing tip.

The distal portion of a catheter 910 including an electrically sensing tip 930 positioned at the distal end of an elongate shaft 912 is shown in FIG. 12. The electrically sensing tip 930 may include one or more layers of electrically conductive ink. For example, a first layer of electrically conductive ink 932 may be positioned next to the distal end of the elongate shaft 912. The electrically conductive ink 932 may be any of those disclosed elsewhere herein. For example, in some embodiments the electrically conductive ink 932 may be an electrically conductive silver or carbon ink. The first layer of electrically conductive ink 932 may be followed distally by one or more layers of a pressure variable resistor ink 934. As shown in FIG. 12, the electrically sensing tip 930 may include two layers of pressure variable resistor ink 934. However, other embodiments may include a single layer of pressure variable resistor ink 934 or three or more layers of pressure variable resistor ink 934, as desired. The electrically sensing tip 930 may include an additional layer of electrically conductive ink 932 distal of the layer(s) of pressure variable resistor ink 934.

The proximal layer of electrically conductive ink 932 adjacent the distal end of the elongate shaft 912 may be electrically connected to a first electrically conductive pathway 920 extending proximally from the electrically sensing tip 930. The distal layer of electrically conductive ink 932 may be electrically connected to a second electrically conductive pathway 920 extending proximally from the electrically sensing tip 930. Thus, an electrical current may be passed across the pressure variable resistor ink layer(s) 934 via the electrical conductive pathways 920 connected to the electrically conductive ink layers 932.

The electrically sensing tip 930 may be used to indicate the pressure experienced at the distal end of the catheter 910 during a medical procedure. For instance, the pressure variable resistor ink layer(s) 934 may be used to indicate the pressure applied to a vessel or lumen wall when the tip 930 is in contact with a patient's vessel or lumen. For instance, during a medical procedure, it may be useful to know the amount of pressure being applied to a vessel or lumen wall as the catheter 910 is being advanced through a patient's vasculature. As shown in FIG. 12, the pressure sensing tip 930 of the catheter 910, including a pressure variable resistor ink layer 934, may be able to provide feedback to an operator concerning what pressure is being experienced at the interface between the pressure sensing tip 930 and the interior surface of the blood vessel. As the pressure experienced at the interface increases or decreases, the electrical resistance across the pressure variable resistor ink layer(s) 934 will be altered. The operator, utilizing an instrument exterior of the patient, may measure the electrical resistance value and/or change in electrical resistance passed through the pressure variable resistor ink layer(s) 934 to determine the pressure experienced at the interface between the pressure sensing tip 930 and the vessel wall.

Figure 13:
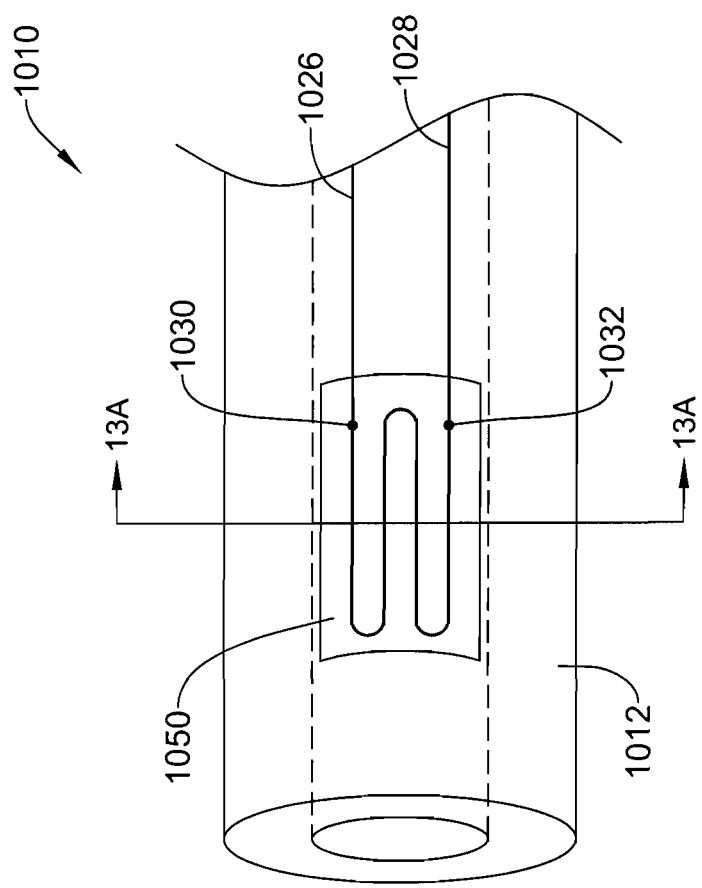
FIG. 13 depicts a distal portion of a catheter including one or more strain gauges.

The distal portion of a catheter 1010 including a strain gauge 1050 positioned near the distal end of an elongate shaft 1012 is shown in FIG. 13. The strain gauge 1050 may be used to sense pressure, strain, torsion, pushing force, and/or deflection experienced at the distal portion of the catheter 1010. A first electrically conductive pathway 1026 extending from a proximal portion of the elongate shaft 1012 may be attached to the first terminal 1030 of the strain gauge 1050 and a second electrically conductive pathway 1028 may be attached to the second terminal 1032 of the strain gauge 1050 to allow an electrical current to pass through the strain gauge 1050.

Figure 13A:
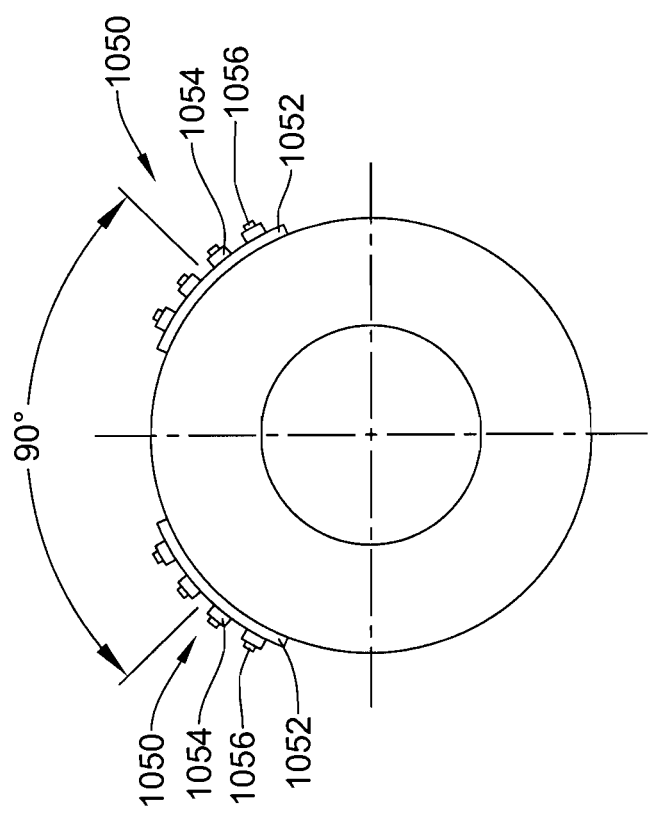
FIG. 13A is a cross-sectional view of the distal portion of the catheter of FIG. 13 taken along line 13A-13A of FIG. 13.

FIG. 13A is a cross-sectional view of the distal portion of the catheter 1010 taken along line 13A-13A of FIG. 13 further illustrating the strain gauge 1050. As shown in FIG. 13A, the distal portion of the catheter 1010 may include two or more strain gauges 1050 to provide directional measurements. For example, a first strain gauge 1050 may be placed about 60°, 90° or 120° away from a second strain gauge 1050. Additional strain gauges 1050 may be utilized as desired. The strain gauge 1050 may include a substrate layer 1052 which is bondable to the elongate shaft 1012. The strain gauge 1050 may then include a serpentine layer of an electrically conductive ink 1054 deposited on the substrate layer 1052. For example, in some embodiments the electrically conductive ink layer 1054 may be an electrically conductive silver or carbon ink which winds back and forth across the substrate layer 1052. The layer of electrically conductive ink 1054 may be overlaid with a serpentine layer of pressure variable resistor ink 1056 following generally the same path as the electrically conductive ink layer 1054. In other embodiments, the strain gauge 1050 may be formed of any other desired materials.

During use, an electrical current/voltage may be passed through the strain gauge 1050 via the electrically conductive pathways 1026/1028 of the elongate shaft 1012. The operator, utilizing an instrument exterior of the patient, may measure the electrical resistance value and/or change in electrical resistance across the strain gauge 1050 to determine the sense pressure, strain, torsion, pushing force, and/or deflection experienced at the distal portion of the catheter 1010.

Figure 14:
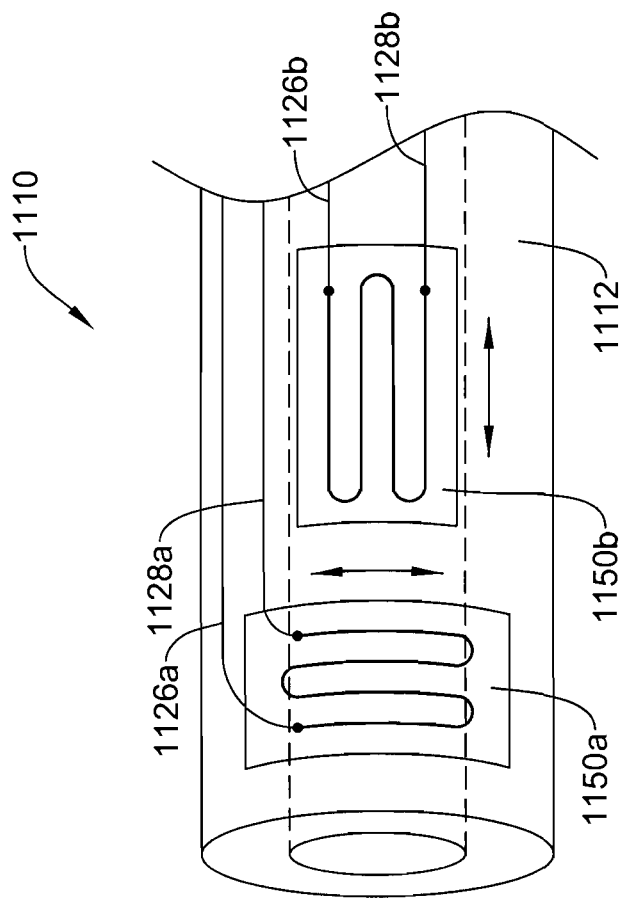
FIG. 14 depicts a distal portion of a catheter including a plurality of strain gauges.

The distal portion of another catheter 1110 including a pair of strain gauges 1150 positioned near the distal end of an elongate shaft 1112 is shown in FIG. 14. The strain gauges 1150 may be of a similar construction to the strain gauge 1050 discussed above. The strain gauges 1150 may be used to sense pressure, strain, torsion, pushing force, and/or deflection experienced at the distal portion of the catheter 1110. For instance, as shown by the arrows in FIG. 14, the first strain gauge 1150a may be used to detect strain transverse to the longitudinal axis of the elongate shaft 1112 near the distal end of the catheter 1110, and the second strain gauge 1150b, rotated 90° relative to the first strain gauge 1150a, may be used to detect strain parallel to the longitudinal axis of the elongate shaft 1112 near the distal end of the catheter 1110. A first electrically conductive pathway 1126a extending from a proximal portion of the elongate shaft 1112 may be attached to a first terminal of the first strain gauge 1150a and a second electrically conductive pathway 1128a may be attached to a second terminal of the first strain gauge 1150a to allow an electrical current to pass through the first strain gauge 1150a. Similarly, a first electrically conductive pathway 1126b extending from a proximal portion of the elongate shaft 1112 may be attached to a first terminal of the second strain gauge 1150b and a second electrically conductive pathway 1128b may be attached to a second terminal of the second strain gauge 1150b to allow an electrical current to pass through the second strain gauge 1150b.

During use, an electrical current/voltage may be passed through the strain gauges 1150 via the electrically conductive pathways 1126/1128 of the elongate shaft 1112. The operator, utilizing an instrument exterior of the patient, may measure the electrical resistance value and/or change in electrical resistance across the strain gauges 1150 to determine the sense pressure, strain, torsion, pushing force, and/or deflection experienced at the distal portion of the catheter 1110. For instance, the first strain gauge 1150a may be used to sense torsional strain of the catheter 1110 and the second strain gauge 1150b may be used to sense longitudinal tension/compression of the catheter 1110.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A medical catheter comprising:
   an extruded elongate tubular member having a central longitudinal axis, the elongate tubular member including an annular wall having an inner surface and an outer surface;
   two or more electrically conductive pathways embedded within the annular wall of the elongate tubular member and extending parallel to the central longitudinal axis of the elongate tubular member from a proximal region of the elongate tubular member to a distal region of the elongate tubular member;
   wherein the annular wall of the elongate tubular member in which the two or more electrically conductive pathways are embedded is a single layer of polymeric material having a continuous molecular structure;
   wherein at least one of the two or more electrically conductive pathways are embedded within the annular wall of the elongate tubular member during an extrusion process;
   wherein at least one of the two or more electrically conductive pathways includes a first electrically conductive element configured to pass an electrical current distally along the tubular member and a second electrically conductive element configured to pass an electrical current proximally along the tubular member.

2. The medical catheter of claim 1, wherein the first and second electrically conductive elements are separate electrically conductive wires.

3. The medical catheter of claim 1, wherein at least one of the one or more electrically conductive pathways includes electrically conductive media;
   wherein the electrically conductive media includes metallic particles deposited in a non-conductive medium.

4. The medical catheter of claim 3, wherein the non-conductive medium of the electrically conductive media is a polymeric material.

5. The medical catheter of claim 3, wherein the electrically conductive media is a metal colloid.

6. The medical catheter of claim 1, further comprising an inner layer of material in contact with the inner surface of the elongate tubular member.

7. The medical catheter of claim 1, further comprising an outer layer of material in contact with the outer surface of the elongate tubular member.

8. The medical catheter of claim 1, wherein the first electrically conductive element is a tubular element and the second electrically conductive element is disposed within the tubular element.

9. The medical catheter of claim 8, further comprising insulation disposed between the tubular element and the second electrically conductive element.

10. A medical catheter comprising:
    an elongate shaft having a proximal end and a distal end;
    an electrically activated/responsive working element located on the elongate shaft and proximate the distal end of the elongate shaft;
    an electrically conductive pathway extending along the exterior of the elongate shaft from a proximal region of the elongate shaft proximate the proximal end of the elongate shaft to a distal region of the elongate shaft proximate the distal end of the elongate shaft;
    the electrically conductive pathway comprising a layer of an electrically conductive ink applied along the elongate shaft; and
    an inflation balloon secured to the elongate shaft, wherein the layer of an electrically conductive ink extends along an exterior surface of the inflation balloon;
    wherein electrical current may be supplied to the electrically activated/responsive working element by the electrically conductive pathway;
    wherein the electrically activated/responsive working element is located distal of the inflation balloon.

11. The medical catheter of claim 10, wherein the electrically activated/responsive working element is spaced distally from a distal end of the inflation balloon.

12. The medical catheter of claim 10, wherein the electrically conductive ink includes a pressure variable resistor ink.

\* \* \* \* \*

UNITED STATES PATENT AND TRADEMARK OFFICE
CERTIFICATE OF CORRECTION

PATENT NO. : 8,734,437 B2  
APPLICATION NO. : 12/178451  
DATED : May 27, 2014  
INVENTOR(S) : James M. Anderson et al.

Page 1 of 1

It is certified that error appears in the above-identified patent and that said Letters Patent is hereby corrected as shown below:

In the Specification

Column 10  
Line 50: after "above 50° C", delete "."  
Line 50: after "above 75° C", delete "."  
Line 51: after "above 100° C", delete "."  
Line 51: after "above 125° C", delete "."  
Line 51: after "above 150° C", delete "."

Signed and Sealed this  
Twenty-ninth Day of July, 2014

Michelle K. Lee  
*Deputy Director of the United States Patent and Trademark Office*